(12) United States Patent
Lee et al.

(10) Patent No.: US 9,193,984 B2
(45) Date of Patent: Nov. 24, 2015

(54) METHOD FOR DETECTING INTERACTIONS BETWEEN TWO AND MORE BIOLOGICAL MACROMOLECULES

(71) Applicant: Korea Basic Science Institute, Daejeon (KR)

(72) Inventors: Zee Won Lee, Daejeon (KR); Soo Hyun Kim, Daejeon (KR)

(73) Assignee: Korea Basic Science Institute, Daejeon (KR)

( * ) Notice: Subject to any disclaimer, the term of this patent is extended or adjusted under 35 U.S.C. 154(b) by 76 days.

(21) Appl. No.: 13/733,687

(22) Filed: Jan. 3, 2013

(65) Prior Publication Data
US 2013/0130273 A1 May 23, 2013

Related U.S. Application Data

(63) Continuation-in-part of application No. 12/547,043, filed on Aug. 25, 2009, now abandoned.

(30) Foreign Application Priority Data

Nov. 12, 2008 (KR) ........................ 10-2008-0112354

(51) Int. Cl.
*G01N 33/53* (2006.01)
*C12Q 1/02* (2006.01)
*G01N 33/50* (2006.01)
*G01N 33/542* (2006.01)
*G01N 33/557* (2006.01)
*C12N 15/10* (2006.01)

(52) U.S. Cl.
CPC ............ *C12Q 1/025* (2013.01); *C12N 15/1055* (2013.01); *G01N 33/5035* (2013.01); *G01N 33/542* (2013.01); *G01N 33/557* (2013.01); *C07K 2319/01* (2013.01); *C07K 2319/60* (2013.01)

(58) Field of Classification Search
CPC ...................................................... G01N 33/53
See application file for complete search history.

(56) References Cited

U.S. PATENT DOCUMENTS 7,282,347 B2 * 10/2007 Bjorn et al. .................... 435/7.6

OTHER PUBLICATIONS

Fu et al, Detection of constitutive heterodimerization of the integrin Mac-1 subunits by fluorescence resonance energy transfer in living cells. Biochem Biophys Res Commun. Aug. 4, 2006;346(3):986-91. Epub Jun. 12, 2006.*

* cited by examiner

*Primary Examiner* — Sheridan Swope
(74) *Attorney, Agent, or Firm* — Mintz Levin Cohn Ferris Glovsky and Popeo, P.C.; Kongsik Kim; Richard B. Emmons

(57) ABSTRACT

Disclosed is a novel method for detecting interactions of biomolecules. More particularly, the disclosed method includes (a) preparing a cell comprising (i) a first construct comprising a bait, a first labeling material and a translocation module; and (ii) a second construct comprising a prey and a second labeling material; (b) detecting the distribution of the first construct and the second construct in the cell. the present invention provides a method capable of detecting bindings and interactions occurring in a living cell in real time, and a method for screening a material that alters the binding and the interaction. The method of the present invention overcomes the disadvantages including inaccuracy and complexity of existing biomaterial interaction detection techniques. By labeling both constructs to promote accuracy, the present invention provides a novel real-time, antibody-free analysis.

5 Claims, 17 Drawing Sheets
(15 of 17 Drawing Sheet(s) Filed in Color)

ized. Accordingly, the present invention provides a novel method enabling the detection of bait and a prey which interact with each other.
METHOD FOR DETECTING INTERACTIONS BETWEEN TWO AND MORE BIOLOGICAL MACROMOLECULES

CROSS-REFERENCE TO RELATED APPLICATIONS

This is a Continuation-In-Part application of U.S. application Ser. No. 12/547,043 filed Aug. 25, 2009, now abandoned, which claim priority to Korean Application No. 10-2008-0112354 filed Nov. 12, 2008, patented Mar. 12, 2010, which applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 2, 2013, is named 84724-CIP-307161_ST25.txt and is 57,284 bytes in size.

TECHNICAL FIELD

Disclosed is a novel method for detecting interactions of biomolecules. More particularly, the disclosed method includes (a) preparing a cell comprising (i) a first construct comprising a bait, a first labeling material and a translocation module; and (ii) a second construct comprising a prey and a second labeling material; (b) detecting the distribution of the first construct and the second construct in the cell.

BACKGROUND

Growth, differentiation, migration, death and the like of cells are mediated by macromolecular interactions such as protein-protein or protein-nucleic acid interactions. Signals from outside of cells pass through receptors located on the cellular membrane and are transmitted to the nucleus of a cell through various biochemical reactions, where they express specific genes. This transfer of external signals into a cell is accomplished by protein interactions of several stages. For example, growth factors or cytokines bind to corresponding cell-surface receptors. This binding induces the receptors to cluster. The clustering of receptors by ligands induces clustering of the intracellular domains of the receptors, thereby causing interactions with signaling-related proteins. Through this signaling mechanism, intermediate proteins capable of transferring signals are produced by phosphorylation by protein kinases, dephosphorylation by protein phosphatases, or the like. As a result, the signals are transmitted to transcriptional activator proteins (Helden, C. H., (1995) *Cell* 80, 213-223). The activated transcriptional activators bind to DNAs and interact with basal transcriptional regulator proteins such as RNA polymerases to activate specific genes. Such interactions enable transcription to occur specifically in specific tissues during embryologic processes or in response to external stimulations. Abnormal modification, inhibition or acceleration of such interactions between specific proteins, which may caused by intrusion of foreign matters, genetic modification of internal activator proteins, or the like, may be the cause of a disorder. Accordingly, there have been consistent researches because substances that can regulate the interactions may provide a way to treat the disorder.

The methods for analyzing the interactions of biomolecules, particularly the binding properties thereof, include traditional in vitro methods such as cross-linking, affinity chromatography, immunoprecipitation (IP), or the like. These methods require the production, isolation and purification of protein and are disadvantageous in that an information different from the actual interaction may be obtained depending on the buffer condition in the test tube, the secondary modification of extracted proteins, or the like.

In order to make up for these drawbacks of the in vitro methods, in-cell methods such as yeast two-hybrid (Y2H), fluorescence resonance energy transfer (FRET) and bimolecular fluorescence complementation (Bi-FC) techniques have been developed. These methods have advantages and disadvantages mentioned below.

Y2H is currently the most widely used technique along with immunoprecipitation. It is advantageous in that large-scale screening is possible using a gene library, but is disadvantageous in that investigation of membrane proteins or nuclear proteins such as transcriptase is difficult and there is a high probability of false positive. Besides, this method is inappropriate to find a substance capable of regulating protein-protein interactions. In the Y2H technique, the interaction between two proteins is detected based on the color change of colony to blue as X-gal is decomposed when β-galactosidase is expressed by the reporter gene. Since the screening technique of detecting the color change from blue back to white by a candidate substance is a negative screening, it is probable that a substance which has actually an inhibitory effect may be unnoticed. Further, since the detection itself is somewhat ambiguous, the technique is not suitable for general drug screening.

The FRET method provides good accuracy, but it is disadvantageous in that positioning of fluorescent proteins or fluorescent materials, which is required for the fluorescence resonance energy transfer to occur, is difficult, thereby having low rate of experimental success. The Bi-FC method is advantageous in that it is applicable to membrane proteins or nuclear proteins. However, like the FRET method, it is disadvantageous in that relative positioning of proteins for complementary binding is difficult, thereby having low rate of success.

Therefore, various modified methods have been proposed to overcome the disadvantages of the above-described methods. However, there is a consistent need for an effective method for detecting the binding of biomaterials. Particularly, a detecting system enabling the detection of proteins interacting with target proteins and enabling a more efficient detection of regulator materials that inhibit or promote the interactions between two proteins is urgently needed.

SUMMARY OF THE DISCLOSURE

The inventors of the present invention have researched to develop a method enabling the real-time detection of binding and interactions of materials in living cells. As a result, we have found that the interaction of a bait and a prey in a living cell can be detected in real time by using a first construct which includes a translocation module moving to a specific region in a cell in response to an external signal or via an internal signaling mechanism and a bait which is a target of an interaction, and a second construct which includes a prey which is another target of the interaction. The first construct and the second construct are labeled with a labeling material, so that the interaction of the bait and the prey in a living cell can be detected in real time by tracing their movements in the cell.

Accordingly, the present invention provides a novel method enabling the detection of bait and a prey which interact with each other.

To achieve the above object, the present invention provides the method for detecting interactions between bait and prey comprising the steps of:

(a) preparing a cell comprising (i) a first construct comprising a bait, a first labeling material and a translocation module; and (ii) a second construct comprising a prey and a second labeling material; and (b) detecting the distribution of the first construct and the second construct in the cell.

To achieve another object, the present invention provides the screening method for materials changing interaction between bait and prey comprising the steps of:

(a) preparing a cell comprising (i) a first construct comprising a bait, a first labeling material and a translocation module; and (ii) a second construct comprising a prey and a second labeling material;

(b) allowing the bait of the first construct and the prey of the second construct to interact;

(c) treating with a signaling material to translocate the first construct to a plasma membrane of the cell; and (d) detecting a translocation of the first construct and the second construct to a plasma membrane of the cell in the cell.

To achieve another object, the present invention provides the cells comprising (i) a first construct comprising bait, a first labeling material and a translocation module; and (ii) a second construct comprising a prey and a second labeling material.

To achieve another object, the present invention provides the kit for detecting interactions between bait and prey comprising the said cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other aspects, features and advantages of the disclosed exemplary embodiments will be more apparent from the following detailed description taken in conjunction with the accompanying drawings in which:

FIG. 1 illustrates basic constructs and analysis indices of the present invention. 1) A first construct comprises a translocation module, a first labeling material and a bait. The first construct may comprise a single bait or a plurality of baits. 2) A second construct comprises a second labeling material and a prey. The second construct may comprise a single prey or a plurality of baits. 3) A signal S includes an extrinsic stimulation inducing the movement of the translocation module, intrinsic stimulation (DAG), and cellular concentration change of ATP or calcium intrinsically or extrinsically. 4) Interaction analysis indices include the distribution of the position of the first construct and second construct by the intrinsic or extrinsic characteristics of baits or preys, change of the distribution, translocation characteristics of the constructs, identification of complexes formed by one or more of the first and second constructs, or the like.

DETAILED DESCRIPTION OF THE DISCLOSURE

Figure 1:
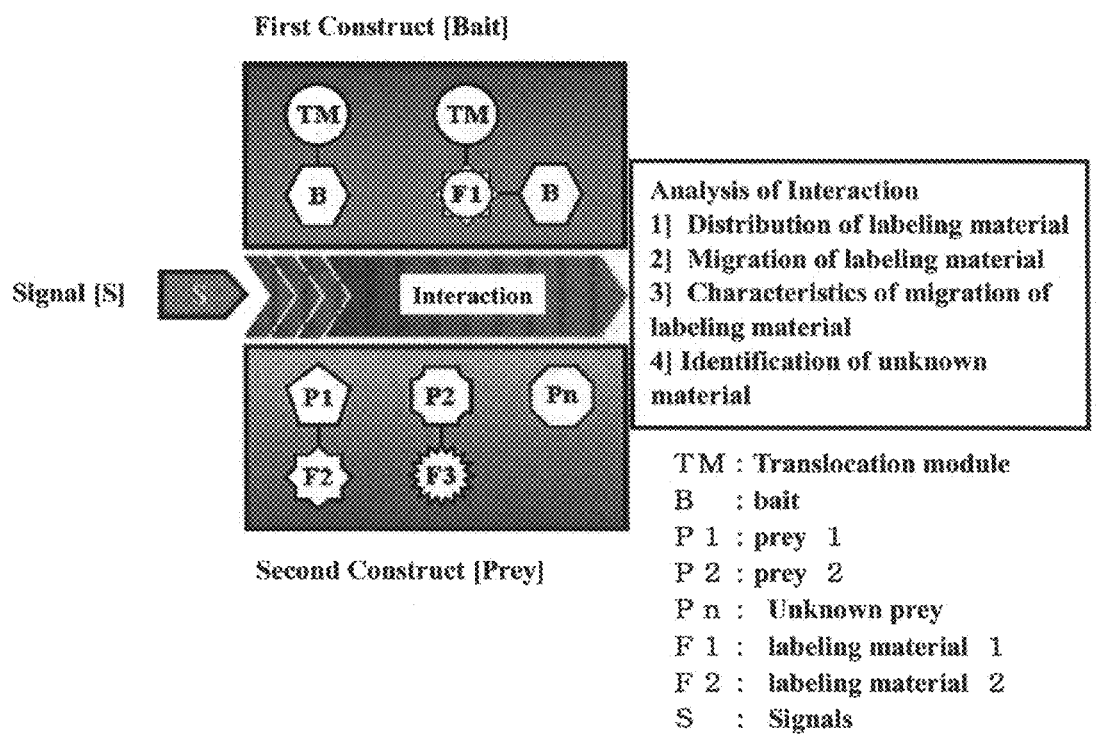

In the present invention, translocation of proteins in a cell in response to an external signal or via an internal signaling mechanism is monitored to detect the interaction between biomaterials in a cell directly and in real time. A first construct is designed by fusing a bait, which is a target of an interaction, with a translocation module, which relocates in response to an external signal or via an intrinsic signaling mechanism, and with a labeling material to trace it. Further, a second construct is designed to comprise a prey interacting with the bait and another labeling material enabling tracing thereof. The first construct and the second construct are made to exist in a cell at the same time. As a result, the interaction between them in a cell can be analyzed directly in real time.

Accordingly, the present invention provides the method for detecting interactions between bait and prey comprising the steps of:

(a) preparing a cell comprising (i) a first construct comprising a bait, a first labeling material and a translocation module; and (ii) a second construct comprising a prey and a second labeling material; and (b) detecting the distribution of the first construct and the second construct in the cell.

The present invention may provides the method for detecting interactions between bait and prey comprising the steps of:

(a) preparing a cell comprising (i) a first construct comprising a bait, a first labeling material and a translocation module; and (ii) a second construct comprising a prey and a second labeling material;

(b) allowing the bait of the first construct and the prey of the second construct to interact; and (c) detecting a translocation of the first construct and the second construct to a plasma membrane of the cell in the cell.

As used herein, the bait (i.e., the molecule of interest) and the prey (i.e., the target molecule) refer to the materials that are subject to an interaction. Each of the bait and the prey may be protein, polypeptide, small organic molecule, polysaccharide or polynucleotide, respectively. Preferably, they may be protein or polypeptide. Further, they may be a natural product, synthetic compound, chemical compound or a combination of two or more of them. For the purpose of detection or screening of an interaction, the bait may be a known material and the prey may be an unknown material. But, without being limited thereto, the bait and the prey may be interchangeably included in the first construct or second construct.

As used herein, a first labeling material and a second labeling material refer to a material capable of generating a signal that can be detected by those skilled in the art. Examples may include fluorescent materials, ligands, light-emitting materials, microparticles (or nanoparticles), redox molecules, radioactive isotopes, or the like. As for fluorescent materials, without being limited thereto, fluorescent protein, fluorescin, isothiocyanate, rhodamine, phycoerythrin, phycocyanin, allo phycocyanin, fluorescinisothiocyanate may be used. Among the above materials, as for fluorescent protein, those which are well known in the art may be used. Examples may include GFP (Green Fluorescent Protein); EGFP (Enhanced Green Fluorescent Protein); RFP (Red Fluorescent Protein); mRFP (Monomeric Red Fluorescent Protein); DsRed (*Discosoma* sp. red fluorescent protein); CFP (Cyan Fluorescent Protein); CGFP (Cyan Green Fluorescent Protein); YFP (Yellow Fluorescent Protein); AzG (Azami Green), HcR (HcRed, *Heteractis crispa* red fluorescent protein), BFP (Blue Fluorescent Protein). As for ligands, there is biotin derivative and as for luminescent, without being limited thereto, there are acridinium ester, luciferin, luciferase, or the like. As for microparticles (or nanoparticles), without being limited thereto, there are colloid gold, iron, colored latex and as for redox molecules, without being limited thereto, there are ferrocene, ruthenium complex compounds, biologen, quinine, Ti ion, Cs ion, diimides, 1,4-benzoquinone, hydroquinone. As for radioactive isotopes, without being limited thereto, there are $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, $^{186}$Re or the like. However, any one which could be used for detecting labeling materials can be used as well as the above exampled materials.

Preferably, a first labeling material and a second labeling material of the present invention may fluorescent proteins. More preferably, a first labeling material and a second labeling material of the present invention may GFP; EGFP; RFP; mRFP; DsRed (*Discosoma* sp. red fluorescent protein); CFP (Cyan Fluorescent Protein); CGFP (Cyan Green Fluorescent Protein); YFP (Yellow Fluorescent Protein); AzG (Azami Green), HcR (HcRed, *Heteractis crispa* red fluorescent protein), or BFP (Blue Fluorescent Protein). At this time, it is preferred that a first labeling material and a second labeling material are different for distinction. More preferably, a first labeling material and a second labeling material of the present invention may have an amino acid sequence represented by SEQ ID NO:9 (EGFP) SEQ ID NO:11 (mRFP), SEQ ID NO:13 (AzG) or SEQ ID NO:15 (HcR) or a nucleotide sequence represented by SEQ ID NO:10 (EGFP), SEQ ID NO:12 (mRFP), SEQ ID NO:14 (AzG) or SEQ ID NO:16 (HcR).

In the present invention, the translocation module serves to move the first construct to a specific region in a cell. The translocation to the specific region may be induced by an external signal or induced intrinsically. The specific region in a cell refers to an intracellular structure which is separate, discreet and identifiable. Preferably, the specific region may be membranous (structures such as cell membrane, plasma membrane, nuclear membrane, etc., organelles such as endoplasmic reticulum, Golgi apparatus, mitochondria, lysosome, etc., or other specific regions in a cell.

The translocation module may be different depending on the particular specific region in a cell. Preferably, it may be protein kinase C (PKC), including classical PKCs (cPKCs; PKC-alpha, PKC-beta and PKC-gamma), novel PKCs (nPKCs; PKC-delta, PKC-epsilon, PKC-eta and PKC-theta), atypical PKCs (aPKCs; PKC-zeta and PKC-lambda/iota) and their variants, known in the art. All of them commonly have the C1 domain. When diacylglycerol (DAG) or phorbol ester (TPA or PMA) binds at the C1 domain, they are induced to move toward the cell membrane. Preferably, a variant of PKC may be used as the translocation module of the present invention. More preferably, the variant may be one from which the internal phosphorylation active site of PKC is removed in order to minimize interference caused by the internal signaling mechanism. More preferably, the translocation module of the present invention may have an amino acid sequence of SEQ ID NO: 1 (PRKCD), SEQ ID NO: 3 (TMA), SEQ ID NO: 5 (TMB) or SEQ ID NO: 7 (TMD), or a nucleotide sequence of SEQ ID NO: 2 (PRKCD), SEQ ID NO: 4 (TMA), SEQ ID NO: 6 (TMB) or SEQ ID NO: 8 (TMD).

Figure 7:
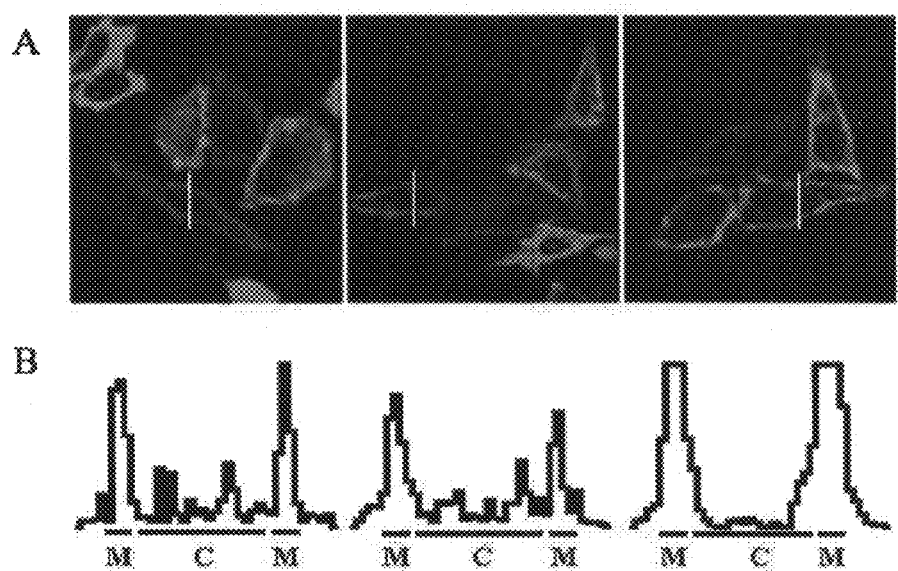
FIG. 7 compares translocation efficiency of the first constructs [TMD-mRFP (right panel), TMA-mRFP (left panel), TMB-mRFP (central panel)]. In order to determine the optimum translocation module for the first construct, translocation efficiency of the first construct vector shown in FIG. 5 (pTMD-mRFP-C3), a pTMA-mRFP-C3 vector comprising a TMD fragment (a vector prepared by inserting TMA translocation module into the mRFP-C3 vector, see Example 2), and a pTMB-mRFP-C3 vector (a vector prepared by inserting TMB translocation module into the mRFP-C3 vector, see Example 2) was evaluated. Detailed experimental procedures were the same as in FIG. 5, All the three constructs exhibited change of distribution in response to an external stimulation (see A). There was no statistical difference in the number of cells with changed distribution. However, when the intensity of fluorescence that moved toward the cell membrane was measured (see white lines in A and B), TMA and TMB showed comparable results, whereas TMD exhibited relatively distinct difference in the cytoplasm (denoted as C) and at the cell membrane (denoted as M). Also, fluorescence density at the cell membrane was higher than those of TMA and TMB. Therefore, all experiments were carried out using TMD which exhibited good translocation characteristic and translocation efficiency.

From the analysis of translocation efficiency of several proteins including RasGRP, which migrates by signals, and C1 domains through preliminary experiments, it was confirmed that full-length PKCs (denoted as PRKCD) or mutants derived from PKC variants (denoted as TMD) of the present invention exhibited relatively superior translocation efficiency (see FIG. 7).

The first construct and second construct expressed may exist in cytosol region of cells. However, the first construct or second construct of the present invention may further include a nuclear localization signal (NLS) or nuclear export signal (NES). These may be further included to control the change of intracellular distribution depending on the intrinsic properties of the bait or prey, or on the particular cell line used in the experiment. In case an NLS is further added, it may direct the first construct and second construct to be distributed uniformly in the nucleus. And, if an NES is further added, it may direct the first construct and second construct to be distributed uniformly in the cytoplasm. Through this, it is possible to recognize whether the binding of the bait and the prey occurs in the cytoplasm or nucleus, or to induce the binding occur in the cytoplasm or nucleus. NLS may preferably have a sequence which is well known in the art (for example, SV40 T Antigen (PKKKRKV), Yeast histone H2B (GKKRSKV), Human c-myc (PAAKRVKLD), Nucleoplasmin (KRPAAT-KKAGQAKKKKL), Human IL-5 (KKYTDGQKKKC-GEERRRVNQ), Human RB (KRSAEGSNPPKPLKKLR), Human p53 (KRALPNNTSSSPQPKKKP)) or the amino acid sequence represented SEQ ID NO:17, more preferably it may have the amino acid sequence represented SEQ ID NO:17 (GSGDEVEGVEEVAKKKSKKEKDK) or the nucleotide sequence represented by SEQ ID NO:18 which encode thereof (ggctctggtgatgaagtcgaaggagtg-gaagaagtagctaagaagaagagtaaaaaggaaaaggataaa). In addition, NES may have a sequence which is well known in the art (for example, Annexin II (VHEILCK-LSLE), mNet (TLWQF-LLH-LLLD), hNet (TLWQF-LLQ-LLLD), MAPKK (ALQKK-LEE-LELD), PKI (ELALK-LAG-LDIN), Rev (LQLPPLER-LTLD), Dsk-1 (SLEGAVSEIS-LR), Cyclin B1 (YLCQAFSDVI-LA), ANXII (STVHEILCK-LSLE), HIV-1 Rev (LQLPPLER-LTLD), MEK-1 (ALQKK-LEE-LELD), PKI-α (ELALK-LAG-LDIN), IkB-α (IQQQLGQ-LTLE), RanBP1 (KBAEKLEA-LSVR), INI1 (DQRVIIKLNAH-VGNISLV)) or amino acid sequence represented SEQ ID NO 19, more preferably it may have the amino acid sequence represented SEQ ID NO:19 (DQRVIIKLNAHVGNISLV) or the nucleotide sequence represented by SEQ ID NO:20 (gac-cagcgcgtcatcatcaagctgaacgcccatgtgggaaacatttccctggtg) which encode thereof.

The detection of the distribution of the first construct and second construct in a cell may be carried out using a labeling material in accordance with a detection method commonly known in the art. For example, if the labeling material is a fluorescent protein, a fluorescence microscope may be used to detect the distribution of the first construct and second construct in a cell.

Initially, both the first construct and second construct are randomly distributed in the cytoplasm or nucleus (a translocation module moving via an intrisic signaling mechanism moves to a specific region. However, targeting to cytosol of each of first construct and second construct without translocation signal is preferred.). When receiving a translocation signal, the first construct is moved toward the cell membrane by the translocation module. At this time, the prey bound to the bait is also carried toward the cell membrane. In contrast, unless the prey is not bound to the bait, its distribution will not change. Accordingly, the binding of the bait and the prey can be recognized by the translocation of the prey toward the cell membrane (see FIGS. 2 and 3). Therefore, translocation of the second construct to the plasma membrane of the cell indicates interactions of the bait and the prey, since the second construct does not have intrinsic translocation module.

Thus, the method of the present invention enables real-time monitoring of direct binding or complex of biomolecules in a living cell through imaging, and provides the following advantages over existing techniques.

1) All bindings occurring in a living cell can be analyzed.
2) Analysis in tissue or individual level is possible.
3) Applicable to animal cells, yeast and bacteria.
4) No antibodies for the bait and prey are required.
5) Accurate analysis is possible because the positional change in a cell is monitored, differently from other methods where the whole cell is monitored.
6) 3-dimensional analysis is unnecessary because 2-dimensional positional change is analyzed.
7) It is not necessary to use the expensive confocal microscope because 3-dimensional analysis is unnecessary.
8) Binding analysis is possible for various cell organelles.
9) Not influenced by external environment as in the in vitro method, because binding occurring in a living cell is monitored.
10) The binding of a bait and a prey can be monitored in real time.
11) The binding of a bait with multiple preys can be monitored.
12) False positive can be minimized through all-or-none monitoring.
13) Interfering bindings due to inflow of extracellular material can be excluded ultimately by using only genes of a bait and a prey and stimulating materials.
14) Complementary screening of protein binding is possible through various modifications of the translocation module.
15) Detection of permanent binding, transient binding and instantaneously occurring interaction is possible.
16) Targets of currently developed signaling inhibitors can be specified.
17) Re-evaluation of inhibitors (drug repositioning/repurposing) is possible through target specification of inhibitor.
18) Screening of binding of a prey to an unknown biomaterial is possible using a mass marker library for the prey.
19) A high-throughput system can be implemented in association with a high-content screening (HCS) system.
20) Simple analysis is possible based on stimulation-free movement.
21) Binding properties can be analyzed for different signaling pathways by changing external stimulation.
22) Relative quantitation of the bait and prey is possible by labeling both the first construct and second construct with a labeling material.
23) False positive or false negative responses can be significantly reduced because the experimental errors related to the translocation of the prey in response to external stimulation or via intrinsic signaling mechanism can be simultaneously verified.

As described, the translocation module may move to a specific region in a cell in response to an external signal. Accordingly, the detection of an interaction between a bait and a prey in accordance with the present invention may further comprise treating with a signaling material. That is, the method may comprise:

(a) preparing a cell comprising (i) a first construct comprising a bait, a first labeling material and a translocation module; and (ii) a second construct comprising a prey and a second labeling material;
(b) allowing the bait of the first construct and the prey of the second construct to interact;
(c) treating with a signaling material to translocate the first construct to a plasma membrane of the cell; and
(d) detecting a translocation of the first construct and the second construct to a plasma membrane of the cell in the cell.

The signaling material refers to a material which generates an external signal inducing the translocation of the translocation module. For example, if PKC is used as the translocation module, the signaling material may be phorbol-12-myristate 13-acetate (PMA; phorbol ester), 12-O-tetradecanoylphorbol-13-acetate (TPA), phorbol-12,13-dibutyrate (PDBu), adenosine triphosphate (ATP), tridecanoic acid, arachidonic acid, linoleic acid, DiC8, 130C937, PKC activation-related growth factors or other PKC activating materials.

PMA may be treated at a concentration of preferably 50 nM to 5 µM, more preferably 1 µM. If the PMA concentration is below 50 nM, translocation of the PKC translocation module may be insufficient. Otherwise, if it exceeds 5 µM, excessive treatment of the chemical may result in undesired phenomena as cell death, signaling interference, or the like.

Also, the present invention provides the method for screening materials which alter interactions of bait and prey comprising the steps of:

(a) preparing a cell including (i) a first construct including a bait, a first labeling material and a translocation module; and (ii) a second construct including a prey and a second labeling material;
(b) treating with a test agent; and
(c) detecting the distribution of the first construct and the second construct in the cell.

As used herein, the term "test agent" includes any substance, molecule, element, compound, entity or a combination thereof. For example, it includes protein, polypeptide, small organic molecule, polysaccharide, polynucleotide, or the like, but is not limited thereto. Further, it may be a natural product, synthetic compound or chemical compound, or a combination of two or more of them. Unless specified otherwise, the terms agent, substance, material and compound may be used interchangeably.

The test agent screened or identified by the method of the present invention may comprise polypeptide, beta-turn mimetics, polysaccharide, phospholipid, hormone, prostaglandin, steroid, aromatic compound, heterocyclic compound, benzodiazepines, oligomeric N-substituted glycines, oligocarbamates, saccharides, fatty acid, purine, pyrimidine or derivatives thereof, structural analogues or mixtures thereof. The said test agent may be derived from broad and various origins which comprise artificial synthesis or library of natural compounds. Preferably, the said test agent may be peptide of, for example, about 5-30, preferably 5-20, more preferably 7-15 amino acids. The said peptide may be naturally generated protein, random peptide, or fragment of "biased" random peptide.

In addition, the said test agent may be "nucleic acid". The nucleic acid test agent may be naturally generated nucleic acid, random nucleic acid, or "biased" random nucleic acid. For example, the fragment of prokaryotic genome or eukaryotic genome may be used as described above.

Further, the test agent may be a small compound molecule (e.g., a molecule having a molecular weight of about 1,000 or smaller). Preferably, high throughput assay may be employed to screen a small molecular agent.

The change of the interaction between the bait and the prey may be either an inhibition or enhancement of the interaction. The inhibition of the interaction refers to the inhibition of the binding between the bait and the prey. In the method of the present invention, the inhibition of the interaction, for example, may be determined from the absence (or decrease of frequency, degree or extent) of translocation of the second construct when the test agent is treated, as compared to that comparable to the translocation of the first construct when the test agent is not treated. The enhancement of the interaction refers to the enhancement of the binding between the bait and the prey. In the method of the present invention, the enhancement of the interaction, for example, may be determined from the presence (or increase of frequency, degree or extent) of translocation of the second construct comparable to that of the first construct when the test agent is treated, as compared to the absence of translocation of the second construct when the test agent is not treated.

In addition, the said screening method may further comprise the step of treating with a signaling material. For example, it may be the method comprising the steps of:

(a) preparing a cell comprising (i) a first construct comprising a bait, a first labeling material and a translocation module; and (ii) a second construct comprising a prey and a second labeling material;

(b) allowing the bait of the first construct and the prey of the second construct to interact;

(c) treating with a test agent;

(d) treating with a signaling material to translocate the first construct to a plasma membrane of the cell; and (e) detecting a translocation of the first construct and the second construct to a plasma membrane of the cell in the cell.

However, the step of treating with a signaling material does not need to be performed prior to the step of treating with a test reagent, and the skilled in the art may control the procedures.

In addition, the present invention provides a cell including (i) a first construct including a bait, a first labeling material and a translocation module; and (ii) a second construct including a prey and a second labeling material.

The cell may be a cell of an animal, plant, yeast or bacteria. Preferably, except for bacteria, it may be a cell capable of accepting the first construct introduced from outside well and having well-defined boundaries of cytoplasm, nucleus and organelles. More preferably, the cell may be CHO-k1 (ATCC CCL-61, *Cricetulus griseus*, hamster, Chinese), HEK293 (ATCC CRL-1573, *Homo sapiens*, human), HeLa (ATCC CCL-2, *Homo sapiens*, human), SH-SY5Y (ATCC CRL-2266, *Homo sapiens*, human), Swiss 3T3 (ATCC CCL-92, *Mus musculus*, mouse), 3T3-L1 (ATCC CL-173, *Mus musculus*, mouse), NIH/3T3 (ATCC CRL-1658, *Mus musculus*, mouse), L-929 (ATCC CCL-1, *Mus musculus*, mouse), Rat2 (ATCC CRL-1764, *Rattus norvegicus*, rat), RBL-2H3 (ATCC CRL-2256, *Rattus norvegicus*, rat), MDCK (ATCC CCL-34, *Canis familiaris*). In addition, the cell may be stem cells, cells extracted from tissues and the artificially made mimic cell membrane structure.

The present invention further provides a kit for detecting interaction comprising a cell comprising the first construct and the second construct of the present invention.

The kit of the present invention may further comprise a tool and/or reagent known in the art used for the detection of a labeling material, in addition to the cell comprising the first construct and second construct. The kit of the present invention may further include a tube, well plate, instruction manual, or the like, if necessary.

The experimental procedures, reagents and reaction conditions that can be used in the method of the present invention may be those commonly known in the art and will be readily understood by those skilled in the art.

In the present invention, the cell comprising the first construct and second construct may be prepared by a molecular biology technique known in the art. Although not limited thereto, expression vectors capable of expressing the first construct and the second construct, respectively, or an expression vector capable of expressing both the first construct and second construct may be introduced into a cell, so that the first construct and second construct are expressed by the expression vector(s). To this end, for the first construct, an expression vector comprising a promoter (first promoter) and a nucleotide encoding a bait, a first labeling material and a translocation module, which is operably linked thereto, may be constructed, and, for the second construct, an expression vector comprising a promoter (second promoter) and a nucleotide encoding a prey and a second labeling material, which is operably linked thereto, may be constructed. The two expression vectors may be simultaneously or sequentially introduced into a single cell, so that the first construct and second construct are expressed by the expression vectors. The sequence of the bait, the first labeling material and the translocation module in the nucleotide is not important, as long as the function of the present invention is exerted. The same is true of the nucleotide encoding the prey and the second labeling material.

The "promoter" means a DNA sequence regulating the expression of nucleic acid sequence operably linked to the promoter in a specific host cell, and the term "operably linked" means that one nucleic acid fragment is linked to other nucleic acid fragment so that the function or expression thereof is affected by the other nucleic acid fragment. Additionally, the promoter may include a operator sequence for controlling transcription, a sequence encoding a suitable mRNA ribosome-binding site, and sequences controlling the termination of transcription and translation. Additionally, it may be constitutive promoter which constitutively induces the expression of a target gene, or inducible promoter which induces the expression of a target gene at a specific site and a specific time, and examples thereof include a SV40 promoter, CMV promoter, CAG promoter (Hitoshi Niwa et al., Gene, 108:193-199, 1991; Monahan et al., *Gene Therapy*, 7:24-30, 2000), CaMV 35S promoter (Odell et al., Nature 313:810-812, 1985), Rsyn7 promoter (U.S. patent application Ser. No. 08/991,601), rice actin promoter (McElroy et al., *Plant Cell* 2:163-171, 1990), Ubiquitin promoter (Christensen et al., *Plant Mol. Biol.* 12:619-632, 1989), ALS promoter (U.S. patent application Ser. No. 08/409,297). Also usable promoters are disclosed in U.S. Pat. Nos. 5,608,149; 5,608,144; 5,604,121; 5,569,597; 5,466,785; 5,399,680; 5,268,463; and 5,608,142, etc).

The introduction of expression vector to a cell may be performed by the transfection methods which are well known in the art, for example, calcium phosphate method, calcium chloride method, rubidium chloride method, microprojectile bombardment, electroporation, particle gun bombardment, Silicon carbide whiskers, sonication, PEG-mediated fusion, microinjection, liposome-mediated method, magnetic nanoparticle-mediated method.

Meanwhile, general recombinant DNA and molecular cloning techniques of the present invention are well known in the art and they are well describe in the following references (Sambrook, J., Fritsch, E. F. and Maniatis, T., Molecular Cloning: A Laboratory Manual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987)).

Hereinafter, the embodiments of the present invention will be described in detail with reference to accompanying drawings.

FIG. 1 illustrates basic constructs and analysis indices of the present invention. 1) A first construct comprises a translocation module, a first labeling material and a bait. The first construct may comprise a single bait or a plurality of baits. 2) A second construct comprises a second labeling material and a prey. The second construct may comprise a single prey or a plurality of baits. 3) A signal S includes an extrinsic stimulation inducing the movement of the translocation module [growth factors, serum factors, PMA, etc. that induce the positional change of translocation module], intrinsic stimulation (DAG), and cellular concentration change of ATP or calcium intrinsically or extrinsically. 4) Interaction analysis indices include the distribution of the position of the first construct and second construct by the intrinsic or extrinsic characteristics of baits or preys, change of the distribution, translocation characteristics of the constructs, identification of complexes formed by one or more of the first and second constructs, or the like.

Figure 2:
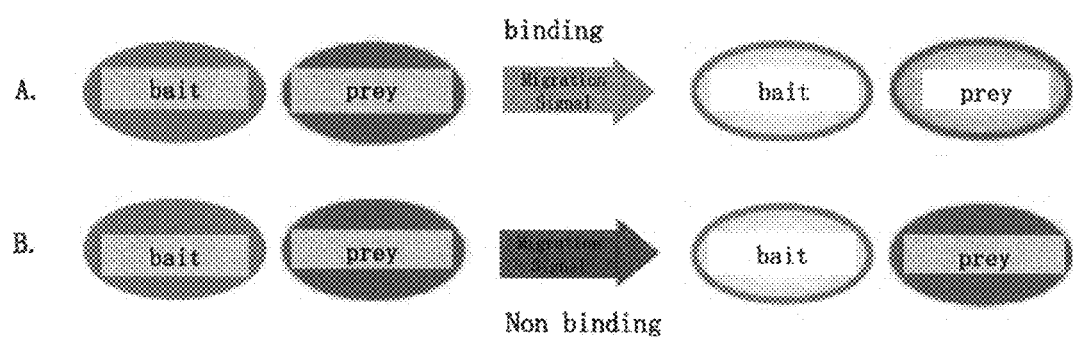
FIG. 2 illustrates a basic concept of binding and non-binding in accordance with the present invention. The bait and prey expressed in the cell are distributed randomly in the cytoplasm or nucleus. In response to a translocation signal, the first construct is carried toward the cell membrane by the translocation module (bait, red). The prey bound to the bait is also carried toward the cell membrane (A; prey, green). In contrast, the prey not bound to the bait does not change its original distribution (B; prey, green). Accordingly, the movement of the prey toward the cell membrane reflects the binding between the bait and prey.

FIG. 2 illustrates a basic concept of binding and non-binding in accordance with the present invention. The bait and prey expressed in the cell are distributed randomly in the cytoplasm or nucleus. In response to a translocation signal, the first construct is carried toward the cell membrane by the translocation module (bait, red). The prey bound to the bait is also carried toward the cell membrane (A; prey, green). In contrast, the prey not bound to the bait does not change its original distribution (B; prey, green). Accordingly, the movement of the prey toward the cell membrane reflects the binding between the bait and prey.

Figure 3:
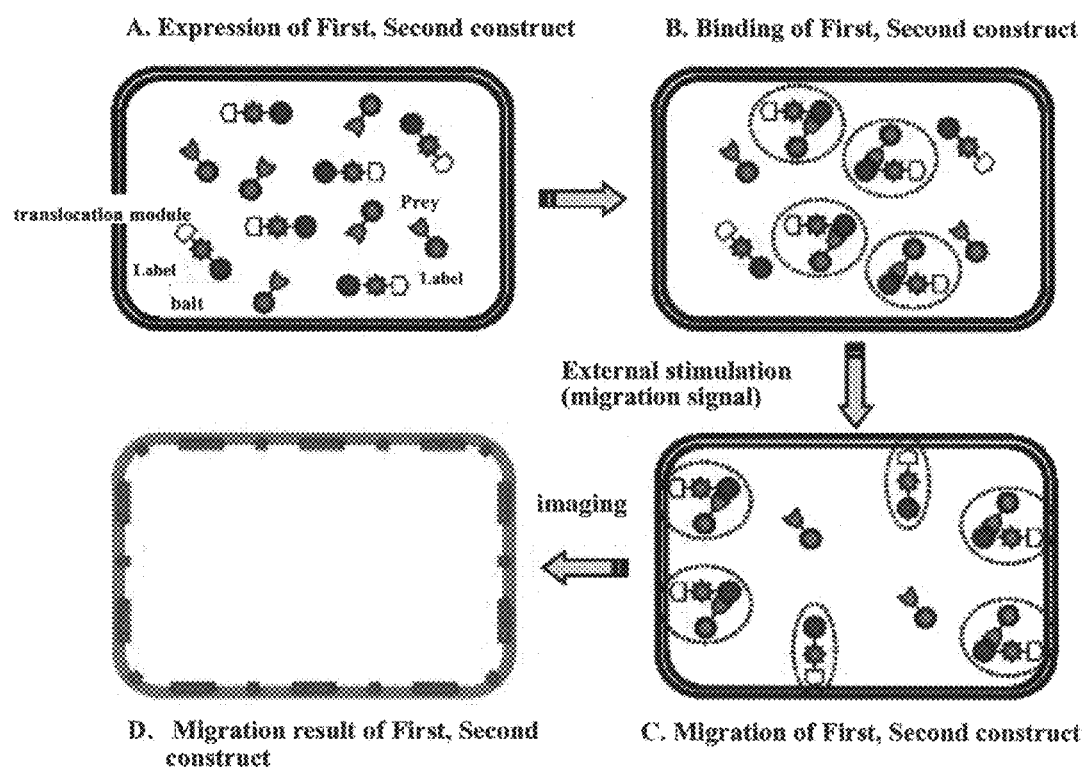
FIG. 3 schematically illustrates the analysis of binding and non-binding in accordance with the present invention. For example, if plasmid vectors wherein the first construct and the second construct are encoded, respectively, are introduced into a cell at the same time, the two constructs are overexpressed in the cell (see A), resulting in the binding of the bait and prey by the intrinsic interaction property. However, in this state, the binding cannot be recognized because the two fluorescent labels exist together as seen in FIG. 2 (see B). When an external stimulation (1 µM PMA) is applied in order to confirm the interaction between baits and preys, the first construct comprising the translocation module moves toward the cell membrane, and the prey bound to the bait is also carried toward the cell membrane (see C). Accordingly, the binding between the bait and prey can be detected from the co-localized translocation of the two fluorescent labels. By labeling both the first construct and second construct with a labeling material and tracing them, the experimental accuracy can be improved as compared to when only the first construct or the second construct is labeled with a labeling material. If only the first construct is labeled with a labeling material, it cannot be confirmed whether the prey binds to the bait. And, if only the second construct is labeled with a labeling material, it cannot be confirmed whether the movement of the prey is due to the binding with the bait, in case the prey has mobility in response to an external stimulation or due to an internal cause.

FIG. 3 schematically illustrates the analysis of binding and non-binding in accordance with the present invention. For example, if plasmid vectors wherein the first construct and the second construct are encoded, respectively, are introduced into a cell at the same time, the two constructs are overexpressed in the cell (see A), resulting in the binding of the bait and prey by the intrinsic interaction property. However, in this state, the binding cannot be recognized because the two fluorescent labels exist together as seen in FIG. 2 (see B). When an external stimulation (1 µM PMA) is applied in order to confirm the interaction between baits and preys, the first construct comprising the translocation module moves toward the cell membrane, and the prey bound to the bait is also carried toward the cell membrane (see C). Accordingly, the binding between the bait and prey can be detected from the co-localized translocation of the two fluorescent labels. By labeling both the first construct and second construct with a labeling material and tracing them, the experimental accuracy can be improved as compared to when only the first construct or the second construct is labeled with a labeling material. If only the first construct is labeled with a labeling material, it cannot be confirmed whether the prey binds to the bait. And, if only the second construct is labeled with a labeling material, it cannot be confirmed whether the movement of the prey is due to the binding with the bait, in case the prey has mobility in response to an external stimulation or due to an internal cause.

Figure 4:
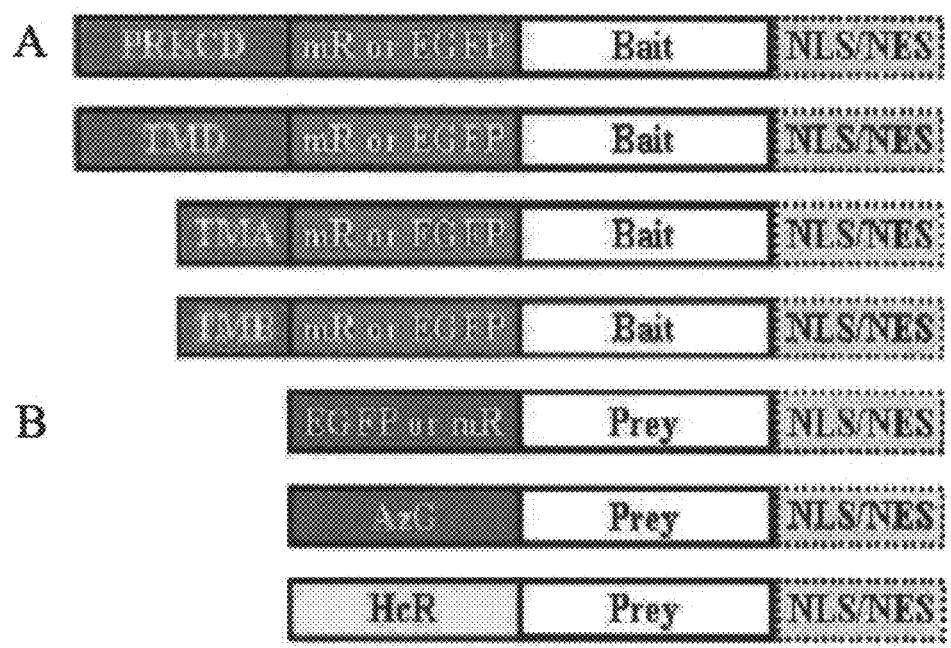
FIG. 4 shows an example of first construct (A) and second construct (B) in accordance with the present invention. Basically, the first construct comprises a translocation module (TMD, TMA, TMB), a fluorescent protein such as red fluorescent protein (mR; mRFP) or green fluorescent protein (EGFP), and a multicloning gene sequence (Bait) for the bait. If it is needed to change the location of the bait or prey in the cell, the construct may further include a nuclear localization signal (NLS) or a nuclear export signal (NES). The second construct comprises a fluorescent protein (any fluorescent protein distinguishable from that of the first construct) for identifying the movement of the prey, and a multicloning gene sequence (Prey) for the prey. The fluorescent protein may be EGFP, mRFP, Azami Green (AzG), HCR, etc. A variety of distinguishable combinations may be attained using currently known fluorescent proteins, depending on the analysis tools (microscope, etc.) to be used.

FIG. 4 shows an example of first construct (A) and second construct (B) in accordance with the present invention. Basically, the first construct comprises a translocation module (TMD, TMA, TMB), a fluorescent protein such as red fluorescent protein (mR; mRFP) or green fluorescent protein (EGFP), and a multicloning gene sequence (Bait) for the bait. If it is needed to change the location of the bait or prey in the cell, the construct may further include a nuclear localization signal (NLS) or a nuclear export signal (NES). The second construct comprises a fluorescent protein (any fluorescent protein distinguishable from that of the first construct) for identifying the movement of the prey, and a multicloning gene sequence (Prey) for the prey. The fluorescent protein may be EGFP, mRFP, Azami Green (AzG), HCR, etc. A variety of distinguishable combinations may be attained using currently known fluorescent proteins, depending on the analysis tools (microscope, etc.) to be used.

Figure 5:
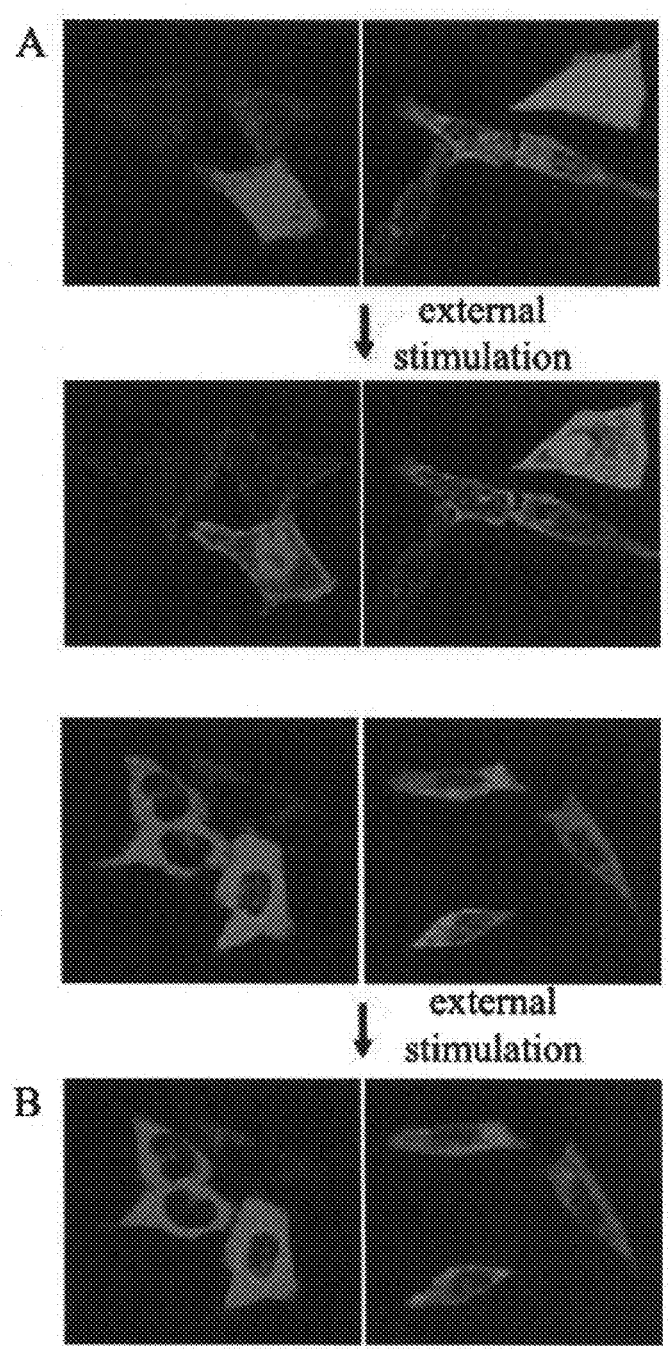
FIG. 5 shows the change of the distribution of the first construct vector and second construct vector in response to an external stimulation. Basic first constructs with no bait cloned (i.e., without a bait) [TMD-EGFP-Bait (A, left panel), TMD-mRFP-Bait (A, right panel)] and basic second constructs with no prey [EGFP-Prey (B, left panel), mRFP-Prey (B, right panel)] were overexpressed in CHO-k1 cell line, and the distribution of the location of the two constructs was confirmed after applying an external stimulation (1 µM PMA). The EGFP- or mRFP-labeled first construct moved toward the cell membrane in response to the external stimulation (see A), whereas the second construct not comprising the translocation module showed no change of fluorescence distribution in response to the external stimulation (see B). Accordingly, it can be seen that the change of the distribution of the second construct is a passive phenomenon occurring due to other factor (the first construct).

FIG. 5 shows the change of the distribution of the first construct vector and second construct vector in response to an external stimulation. Basic first constructs with no bait cloned (i.e., without a bait) [TMD-EGFP-Bait (A, left panel), TMD-mRFP-Bait (A, right panel)] and basic second constructs with no prey [EGFP-Prey (B, left panel), mRFP-Prey (B, right panel)] were overexpressed in CHO-k1 cell line, and the distribution of the location of the two constructs was confirmed after applying an external stimulation (1 µM PMA). The EGFP- or mRFP-labeled first construct moved toward the cell membrane in response to the external stimulation (see A), whereas the second construct not comprising the translocation module showed no change of fluorescence distribution in response to the external stimulation (see B). Accordingly, it can be seen that the change of the distribution of the second construct is a passive phenomenon occurring due to other factor (the first construct).

Figure 6:
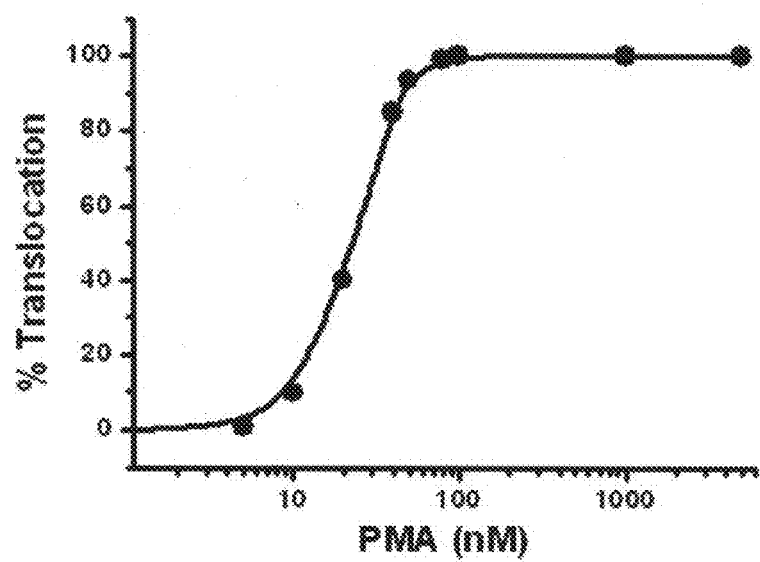
FIG. 6 shows the change of the distribution of the first construct (TMD-mRFP) depending on the PMA concentration. In order to optimize the translocation characteristic of the translocation module, the first construct vector (pTMD-mRFP-C3) shown in FIG. 5 was used to determine the optimum concentration of PMA (phorbol-12-myristate-13-acetate), which was used as an external stimulation. Detailed experimental procedures were the same as in FIG. 5. After treating with PMA at concentrations of 1 nM to 5 µM, the cells in which red fluorescence moved toward the cell membrane were counted among randomly selected fluorescence-exhibiting cells. As seen in the table, IC50 was measured as 35 nM. At 50 nM, 90% or more translocation was observed. At 100 nM or higher concentrations, movement of red fluorescence toward the cell membrane increased. Therefore, all experiments were carried out at 1 µM, which is a concentration sufficient for the response and movement of most cells.

FIG. 6 shows the change of the distribution of the first construct (TMD-mRFP) depending on the PMA concentration. In order to optimize the translocation characteristic of the translocation module, the first construct vector (pTMD-mRFP-C3) shown in FIG. 5 was used to determine the optimum concentration of PMA (phorbol-12-myristate-13-acetate), which was used as an external stimulation. Detailed experimental procedures were the same as in FIG. 5. After treating with PMA at concentrations of 1 nM to 5 µM, the cells in which red fluorescence moved toward the cell membrane were counted among randomly selected fluorescence-exhibiting cells. As seen in the table, $IC_{50}$ was measured as 35 nM. At 50 nM, 90% or more translocation was observed. At 100 nM or higher concentrations, movement of red fluorescence toward the cell membrane increased. Therefore, all experiments were carried out at 1 µM, which is a concentration sufficient for the response and movement of most cells.

FIG. 7 compares translocation efficiency of the first constructs [TMD-mRFP (right panel), TMA-mRFP (left panel), TMB-mRFP (central panel)]. In order to determine the optimum translocation module for the first construct, translocation efficiency of the first construct vector shown in FIG. 5 (pTMD-mRFP-C3), a pTMA-mRFP-C3 vector comprising a TMD fragment (a vector prepared by inserting TMA translocation module into the mRFP-C3 vector, see Example 2), and a pTMB-mRFP-C3 vector (a vector prepared by inserting TMB translocation module into the mRFP-C3 vector, see Example 2) was evaluated. Detailed experimental procedures were the same as in FIG. 5, All the three constructs exhibited change of distribution in response to an external stimulation (see A). There was no statistical difference in the number of cells with changed distribution. However, when the intensity of fluorescence that moved toward the cell membrane was measured (see white lines in A and B), TMA and TMB showed comparable results, whereas TMD exhibited relatively distinct difference in the cytoplasm (denoted as C) and at the cell membrane (denoted as M). Also, fluorescence density at the cell membrane was higher than those of TMA and TMB. Therefore, all experiments were carried out using TMD which exhibited good translocation characteristic and translocation efficiency.

Figure 8:
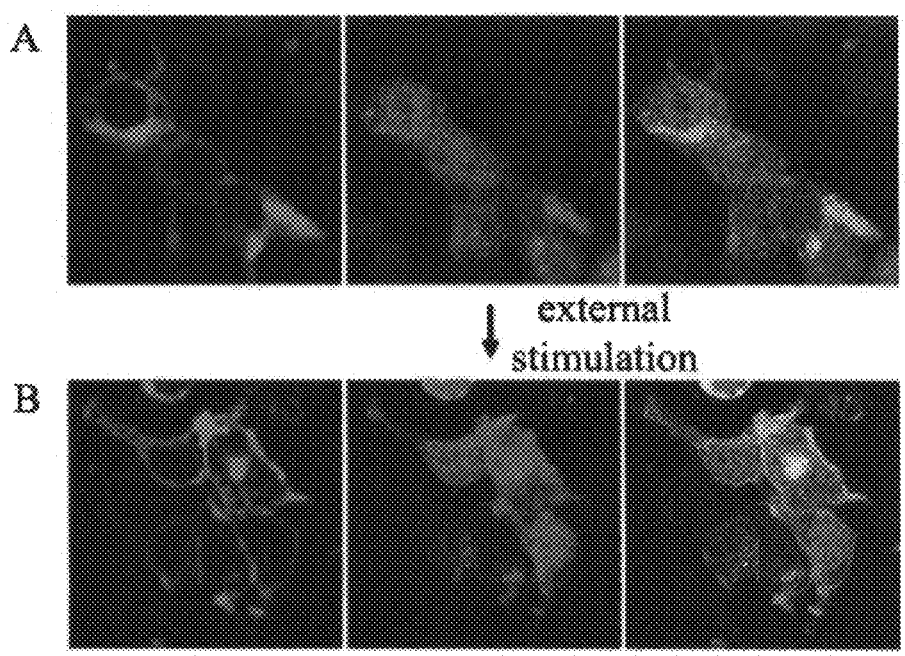
FIG. 8 shows the result of verifying the efficiency of NES sequence which limits the expression site of the first construct to the cytoplasm, in order to promote the efficacy of the present construct. In order to verify the effect of the NES sequence, a first construct (TMD-mRFP-Bait-NES) basic vector comprising the NES sequence (pTMD-mRFP-C3-NES vector) was prepared, and overexpressed in HEK-293 cell line along with a second construct (EGFP-Prey-NES) basic vector (pEGFP-C3-NES vector). The NES sequence-including first construct was observed mainly in the cytoplasm while the second construct was uniformly distributed in the whole cell (see A). After treating with PMA for 3 minutes, the first construct which had been uniformly distributed in the cytoplasm moved toward the cell membrane, whereas the second construct without including the NES sequence did not show any change in distribution (see B; left panel: first construct, central panel: second construct, right panel: merge).

FIG. 8 shows the result of verifying the efficiency of NES sequence which limits the expression site of the first construct to the cytoplasm, in order to promote the efficacy of the present construct. In order to verify the effect of the NES sequence, a first construct (TMD-mRFP-Bait-NES) basic vector comprising the NES sequence (pTMD-mRFP-C3-NES vector) was prepared, and overexpressed in HEK-293 cell line along with a second construct (EGFP-Prey-NES) basic vector (pEGFP-C3-NES vector). The NES sequence-including first construct was observed mainly in the cytoplasm while the second construct was uniformly distributed in the whole cell (see A). After treating with PMA for 3 minutes, the first construct which had been uniformly distributed in the cytoplasm moved toward the cell membrane, whereas the second construct without including the NES sequence did not show any change in distribution (see B; left panel: first construct, central panel: second construct, right panel: merge).

Figure 9:
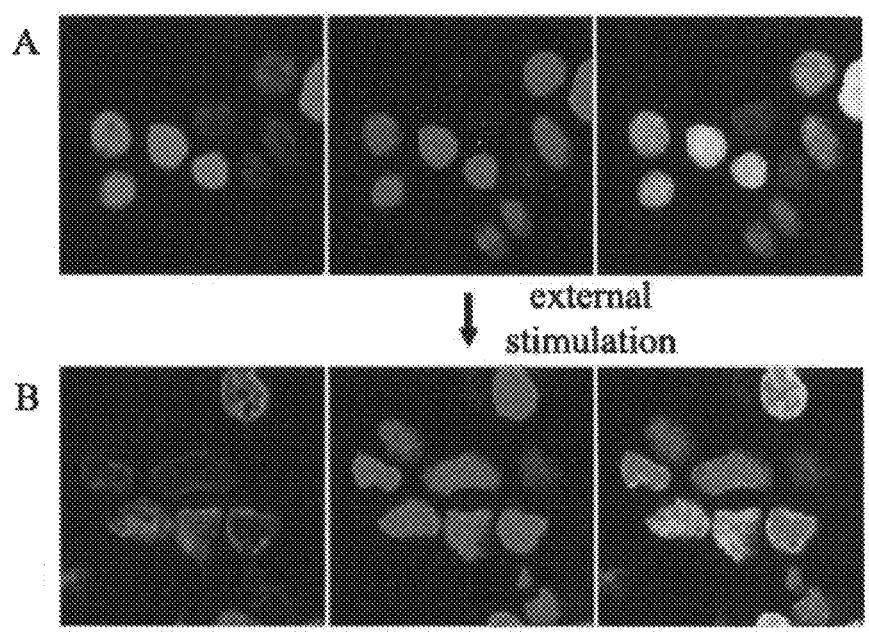
FIG. 9 shows the result of verifying the efficiency of NLS sequence which limits the expression site of the first construct to the nucleus, in order to promote the efficacy of the present construct. In order to verify the effect of the NLS sequence, TMD-mRFP-Bait-NLS (pTMD-mRFP-C3-NLS vector) and EGFP-Prey-NLS (pEGFP-C3-NLS vector) basic vectors were prepared and overexpressed in HEK-293 cell line. The NLS sequence-including first construct and second construct were observed mainly in the nucleus (see A). After treating with PMA for 3 minutes, the first construct and second construct which had been uniformly distributed in the nucleus moved toward the nuclear membrane, whereas the second construct without the translocation module did not show any change in distribution (see B; left panel: first construct, central panel: second construct, right panel: merge).

FIG. 9 shows the result of verifying the efficiency of NLS sequence which limits the expression site of the first construct to the nucleus, in order to promote the efficacy of the present construct. In order to verify the effect of the NLS sequence, TMD-mRFP-Bait-NLS (pTMD-mRFP-C3-NLS vector) and EGFP-Prey-NLS (pEGFP-C3-NLS vector) basic vectors were prepared and overexpressed in HEK-293 cell line. The NLS sequence-including first construct and second construct were observed mainly in the nucleus (see A). After treating with PMA for 3 minutes, the first construct and second construct which had been uniformly distributed in the nucleus moved toward the nuclear membrane, whereas the second construct without the translocation module did not show any change in distribution (see B; left panel: first construct, central panel: second construct, right panel: merge).

Figure 10:
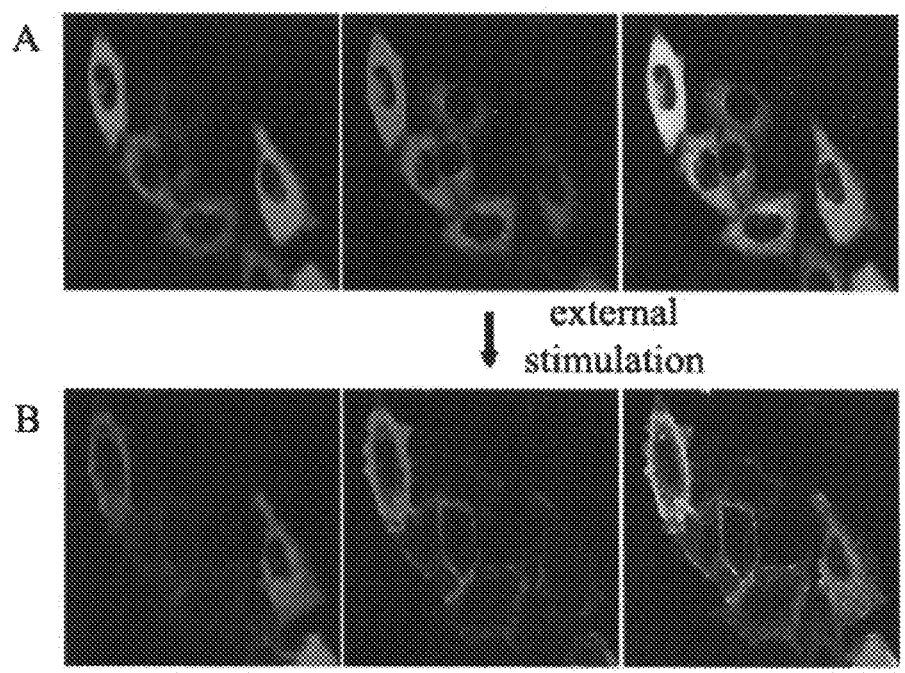
FIG. 10 shows the result of analyzing the binding of p53 protein and SV40T protein using the method of the present invention. In order to verify the binding of the bait (p53 protein) and the prey (SV40T protein), TMD-mRFP-p53 (first construct) and EGFP-SV40T (second construct) were prepared and overexpressed in CHO-k1 cell line. After treating with PMA for 3 minutes, the two proteins which had been uniformly distributed in the cell (A) moved toward the cell membrane (B) (red fluorescence: translocation module+p53 protein, green fluorescence: SV40T protein). Accordingly, it was confirmed that the two proteins are bound to each other in the cell (left panel: first construct, central panel: second construct, right panel: merge).

FIG. 10 shows the result of analyzing the binding of p53 protein and SV40T protein using the method of the present invention. In order to verify the binding of the bait (p53 protein) and the prey (SV40T protein), TMD-mRFP-p53 (first construct) and EGFP-SV40T (second construct) were prepared and overexpressed in CHO-k1 cell line. After treating with PMA for 3 minutes, the two proteins which had been uniformly distributed in the cell (A) moved toward the cell membrane (B) (red fluorescence: translocation module+p53 protein, green fluorescence: SV40T protein). Accordingly, it was confirmed that the two proteins are bound to each other in the cell (left panel: first construct, central panel: second construct, right panel: merge).

Figure 11:
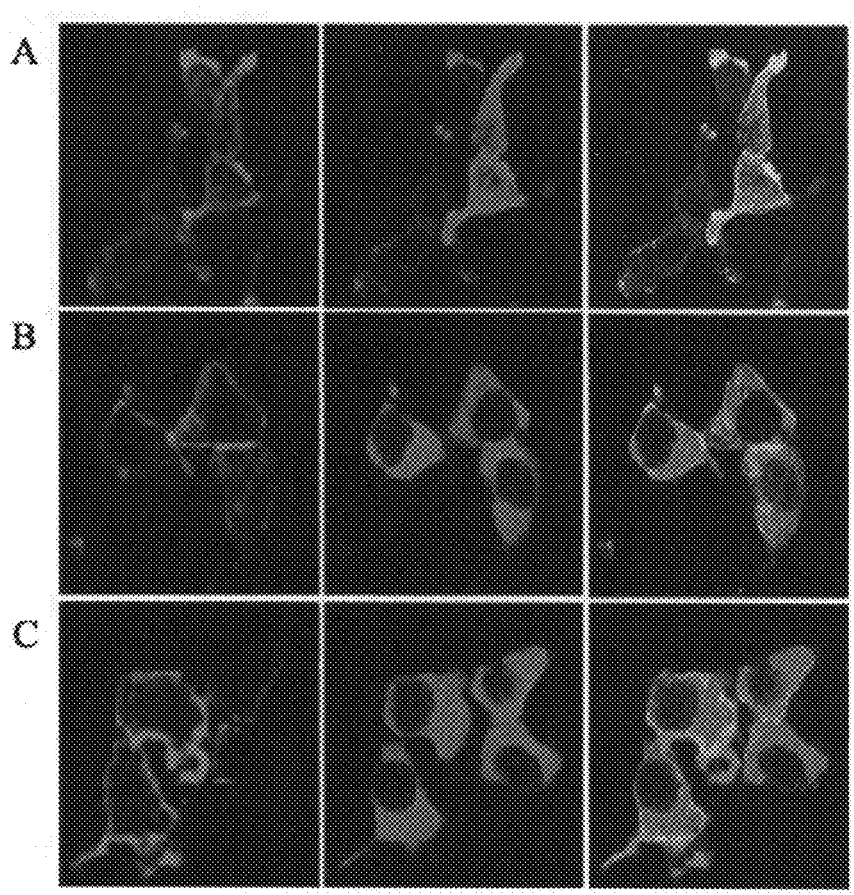
FIG. 11 shows the result of analyzing the binding of lysyl-tRNA synthetase (KRS) and JTV1 (p38), Gag and laminin receptor (LR). In order to verify the binding of p38, Gag and LR, which were expected to bind with the KRS protein, KRS (as second construct) and p38, Gag and LR (as first construct) were overexpressed in HEK-293 cell line. Fluorescence distribution in the cell before and after treatment with PMA was analyzed. (A) TMD-mRFP-p38 and AzG-KRS strongly moved toward the cell membrane in response to an external stimulation, whereas TMD-mRFP-Gag (B) or TMD-mRFP-LR (C) labeled with green fluorescence did not show translocation. Accordingly, it was confirmed that KRS binds with p38 among the three proteins (left panel: first construct, central panel: second construct, right panel: merge).

FIG. 11 shows the result of analyzing the binding of lysyl-tRNA synthetase (KRS) and JTV1 (p38), Gag and laminin receptor (LR). In order to verify the binding of p38, Gag and LR, which were expected to bind with the KRS protein, KRS (as second construct) and p38, Gag and LR (as first construct) were overexpressed in HEK-293 cell line. Fluorescence distribution in the cell before and after treatment with PMA was analyzed. (A) TMD-mRFP-p38 and AzG-KRS strongly moved toward the cell membrane in response to an external stimulation, whereas TMD-mRFP-Gag (B) or TMD-mRFP-LR (C) labeled with green fluorescence did not show translocation. Accordingly, it was confirmed that KRS binds with p38 among the three proteins (left panel: first construct, central panel: second construct, right panel: merge).

Figure 12:
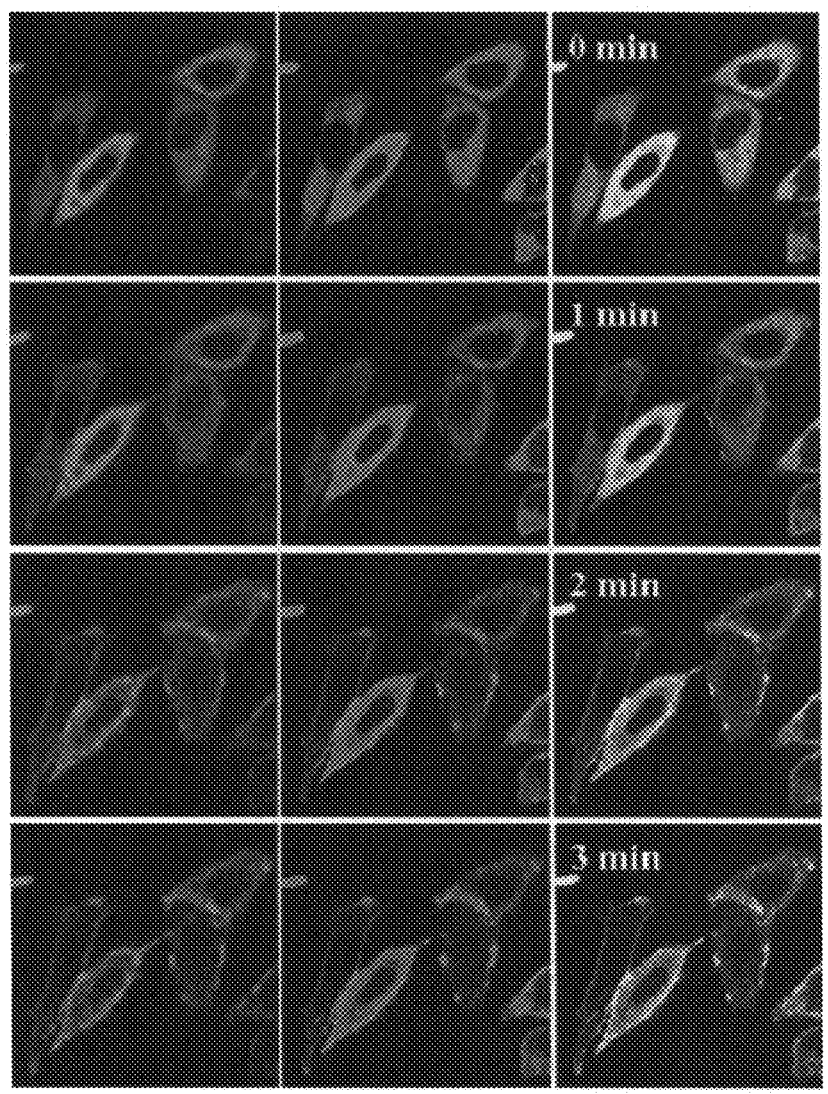
FIG. 12 shows the result of analyzing the binding of RelA and IkB in real time using a confocal laser fluorescence microscope. RelA and IkB, which are known to form a complex in a cell, were prepared into TMD-mRFP-RelA and EGFP-IkB, respectively, and overexpressed in CHO-k1 cell. Images were taken every 10 seconds, using a confocal laser fluorescence microscope. Prior to PMA treatment (0 min), fluorescences of the two proteins were uniformly distributed in the cytoplasm. About 10 seconds to 1 minute after the PMA treatment, the two fluorescences moved toward the cell membrane. Accordingly, it was confirmed that binding of two proteins in a living cell can be analyzed in real time. Hence, the present invention is useful for the study of cell signaling mechanisms in response to various stimulations including translocation signals (left panel: first construct, central panel: second construct, right panel: merge).

FIG. 12 shows the result of analyzing the binding of RelA and IkB in real time using a confocal laser fluorescence microscope. RelA and IkB, which are known to form a complex in a cell, were prepared into TMD-mRFP-RelA and EGFP-IkB, respectively, and overexpressed in CHO-k1 cell. Images were taken every 10 seconds, using a confocal laser fluorescence microscope. Prior to PMA treatment (0 min), fluorescences of the two proteins were uniformly distributed in the cytoplasm. About 10 seconds to 1 minute after the PMA treatment, the two fluorescences moved toward the cell membrane. Accordingly, it was confirmed that binding of two proteins in a living cell can be analyzed in real time. Hence, the present invention is useful for the study of cell signaling mechanisms in response to various stimulations including translocation signals (left panel: first construct, central panel: second construct, right panel: merge).

Figure 13:
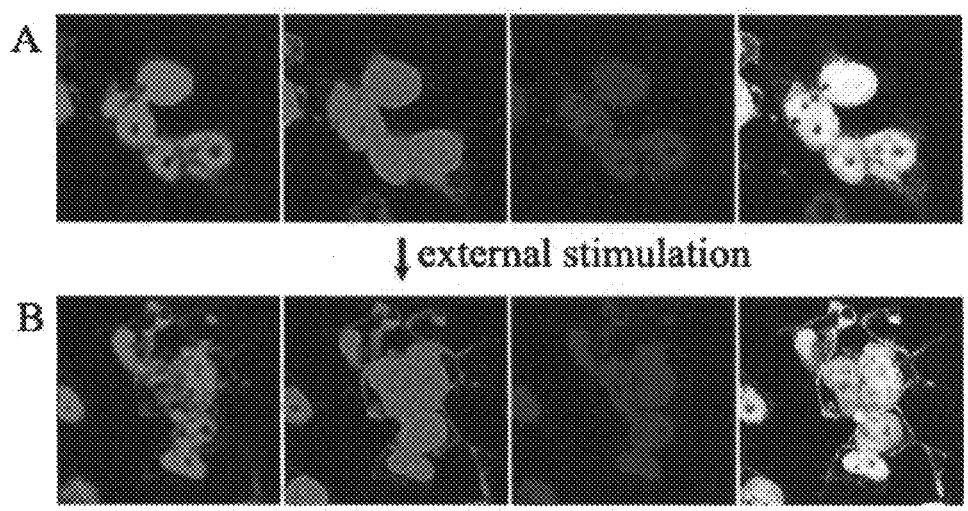
FIG. 13 shows the result of analyzing the binding of three protein complexes. The two proteins (RelA and IkB) of FIG. 12 are known to form an NFkB-IkB complex in a cell along with p50 protein. In order to verify whether the binding of a plurality of proteins can be analyzed, the second construct HcR-p50 was prepared by binding p50 protein with another fluorescent protein HcRed (HcR). The three constructs were overexpressed in HEK-293 cell line and their binding was observed using a confocal laser fluorescence microscope. Fluorescence signals (red, green and blue) reflecting the three proteins were uniformly distributed in the cytoplasm and nucleus prior to PMA treatment (A). However, after the PMA treatment (B), all of them moved toward the cell membrane. This result means that complexes composed of at least three proteins can be analyzed at the same time using the constructs of the present invention [from the left side, first panel: first construct (TMD-mRFP-RelA), second panel: second construct 1 (EGFP-IkB), third panel: second construct 2 (HcR-p50), right panel: merge].

FIG. 13 shows the result of analyzing the binding of three protein complexes. The two proteins (RelA and IkB) of FIG. 12 are known to form an NFkB-IkB complex in a cell along with p50 protein. In order to verify whether the binding of a plurality of proteins can be analyzed, the second construct HcR-p50 was prepared by binding p50 protein with another fluorescent protein HcRed (HcR). The three constructs were overexpressed in HEK-293 cell line and their binding was observed using a confocal laser fluorescence microscope. Fluorescence signals (red, green and blue) reflecting the three proteins were uniformly distributed in the cytoplasm and nucleus prior to PMA treatment (A). However, after the PMA treatment (B), all of them moved toward the cell membrane. This result means that complexes composed of at least three proteins can be analyzed at the same time using the constructs of the present invention [from the left side, first panel: first construct (TMD-mRFP-RelA), second panel: second construct 1 (EGFP-IkB), third panel: second construct 2 (HcR-p50), right panel: merge].

Figure 14:
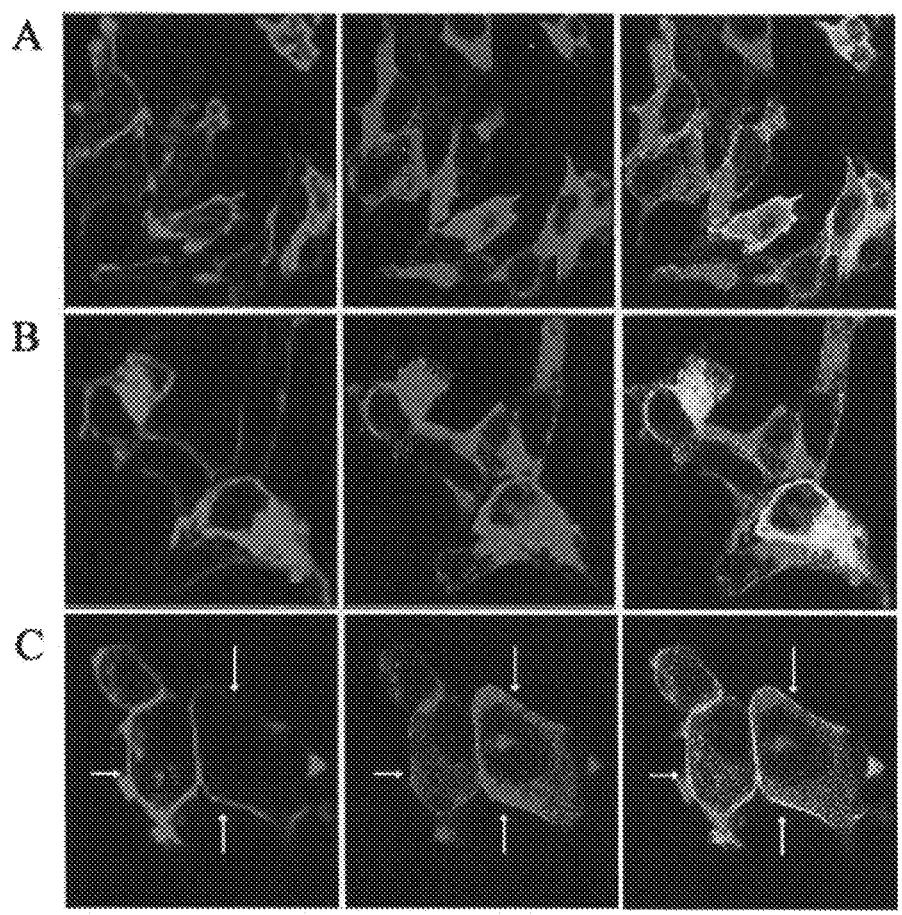
FIG. 14 shows the result of verifying the binding of positive candidates screened through Y2H. In order to reconfirm the binding of the candidates screened through Y2H, a screening method commonly used for screening of protein interaction, a first construct comprising OmpA protein as bait (TMD-mRFP-OmpA) and second constructs comprising EEF1A, FAM14B and DDX31 as prey candidates (EGFP-EEF1A, EGFP-FAM14B and EGFP-DDX31) were prepared. Combination of the bait and each of the prey candidates were overexpressed in HEK-293 cell line and their binding was observed using a confocal laser fluorescence microscope. Fluorescences were uniformly distributed in the cell prior to PMA treatment. After the PMA treatment, the translocation modules binding with the OmpA protein moved toward the cell membrane (red). Of the green fluorescences reflecting the prey candidates that were expected to bind thereto, EEF1A (A) and FAM14B (B) remained in the cytoplasm and DDX31 (C) moved toward the cell membrane. Thus, it was confirmed that only one of the three candidates screened through Y2H participates in the binding. This result shows that the present invention can solve the false positive problem of Y2H (left panel: first construct, central panel: second construct, right panel: merge).

FIG. 14 shows the result of verifying the binding of positive candidates screened through Y2H. In order to reconfirm the binding of the candidates screened through Y2H, a screening method commonly used for screening of protein interaction, a first construct comprising OmpA protein as bait (TMD-mRFP-OmpA) and second constructs comprising EEF1A, FAM14B and DDX31 as prey candidates (EGFP-EEF1A, EGFP-FAM14B and EGFP-DDX31) were prepared. Combination of the bait and each of the prey candidates were overexpressed in HEK-293 cell line and their binding was observed using a confocal laser fluorescence microscope. Fluorescences were uniformly distributed in the cell prior to PMA treatment. After the PMA treatment, the translocation modules binding with the OmpA protein moved toward the cell membrane (red). Of the green fluorescences reflecting the prey candidates that were expected to bind thereto, EEF1A (A) and FAM14B (B) remained in the cytoplasm and DDX31 (C) moved toward the cell membrane. Thus, it was confirmed that only one of the three candidates screened through Y2H participates in the binding. This result shows that the present invention can solve the false positive problem of Y2H (left panel: first construct, central panel: second construct, right panel: merge).

Figure 15:
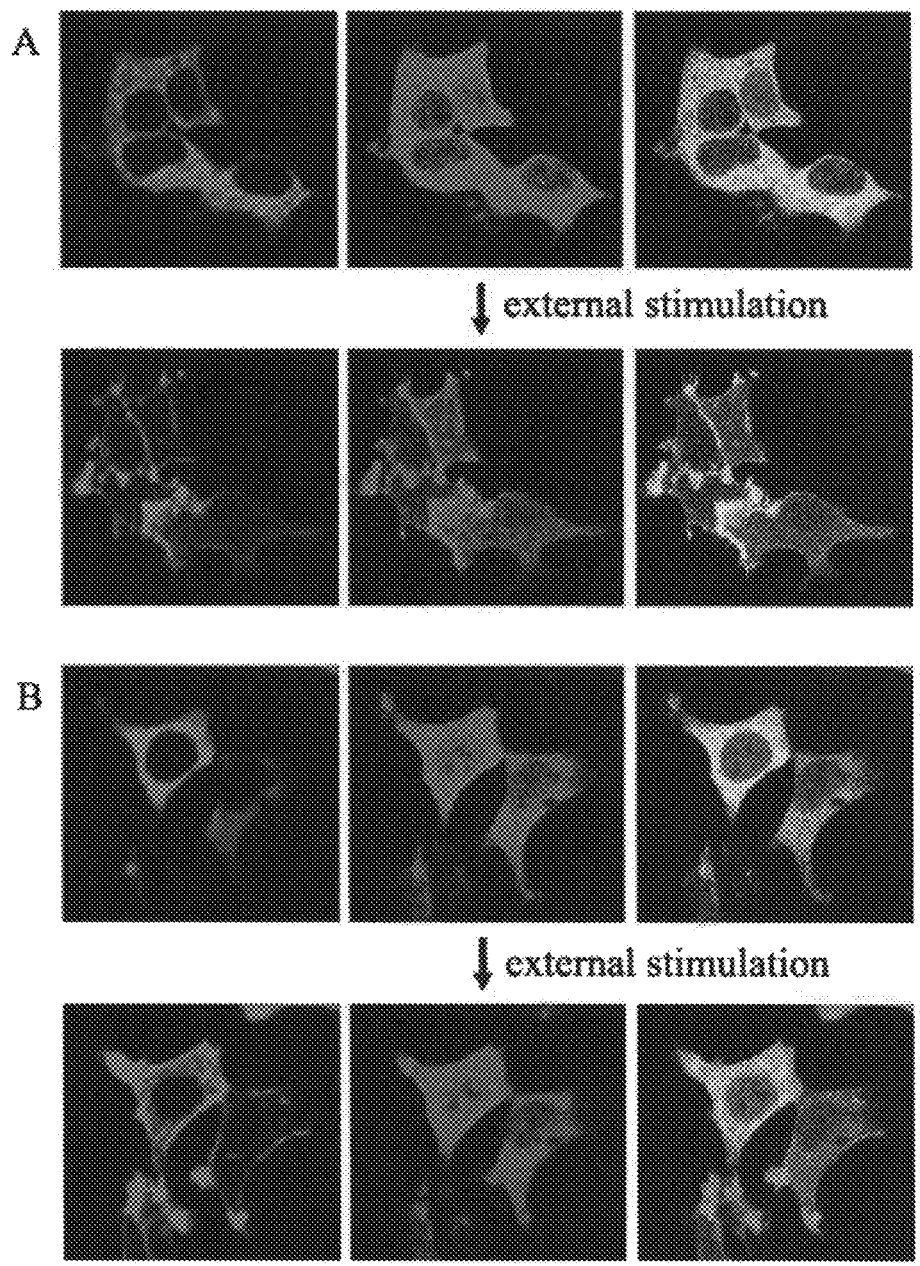
FIG. 15 shows the result of analyzing the binding of p53 protein with mdm2 protein and the inhibition of binding by the anticancer drug nutlin3. In order to verify the effectiveness of the present invention in new drug development, experiments were carried out on the inhibition of binding of an anticancer drug. To this end, a first construct comprising p53 protein (TMD-mRFP-p53N) and a second construct comprising mdm2 protein (AzG-mdm2N) were prepared. The constructs were overexpressed in HEK-293 cell line and their binding was observed using a confocal laser fluorescence microscope. First, in order to verify the binding of p53N and mdm2N, cells not treated with nutlin3 were compared before and after PMA treatment (A). The two proteins which had been uniformly distributed in the cytoplasm prior to the PMA treatment moved toward the cell membrane after the PMA treatment. This indicates that the two proteins are bound to each other. Next, in order to verify the binding inhibition effect of the anticancer drug nutlin3, cells were cultured in a medium containing 20 nM nutlin3 for 20 minutes. Then, fluorescence distribution was observed in real time before and after PMA treatment (B). In the nutlin3-pretreated cells, the first construct (red) comprising the translocation module and p53N moved toward the cell membrane, but the second construct (green) comprising only mdm2N and fluorescent protein with no translocation module did not show translocation toward the cell membrane. Thus, it was confirmed that the present invention is useful in verifying the inhibition of binding of p53 and mdm2 by the anticancer drug nutlin3. Therefore, the present invention can be used to screen inhibitors of binding of proteins or peptides (left panel: first construct, central panel: second construct, right panel: merge).

FIG. 15 shows the result of analyzing the binding of p53 protein with mdm2 protein and the inhibition of binding by the anticancer drug nutlin3. In order to verify the effectiveness of the present invention in new drug development, experiments were carried out on the inhibition of binding of an anticancer drug. To this end, a first construct comprising p53 protein (TMD-mRFP-p53N) and a second construct comprising mdm2 protein (AzG-mdm2N) were prepared. The constructs were overexpressed in HEK-293 cell line and their binding was observed using a confocal laser fluorescence microscope. First, in order to verify the binding of p53N and mdm2N, cells not treated with nutlin3 were compared before and after PMA treatment (A). The two proteins which had been uniformly distributed in the cytoplasm prior to the PMA treatment moved toward the cell membrane after the PMA treatment. This indicates that the two proteins are bound to each other. Next, in order to verify the binding inhibition effect of the anticancer drug nutlin3, cells were cultured in a medium containing 20 nM nutlin3 for 20 minutes. Then, fluorescence distribution was observed in real time before and after PMA treatment (B). In the nutlin3-pretreated cells, the first construct (red) comprising the translocation module and p53N moved toward the cell membrane, but the second construct (green) comprising only mdm2N and fluorescent protein with no translocation module did not show translocation toward the cell membrane. Thus, it was confirmed that the present invention is useful in verifying the inhibition of binding of p53 and mdm2 by the anticancer drug nutlin3. Therefore, the present invention can be used to screen inhibitors of binding of proteins or peptides (left panel: first construct, central panel: second construct, right panel: merge).

Figure 16:
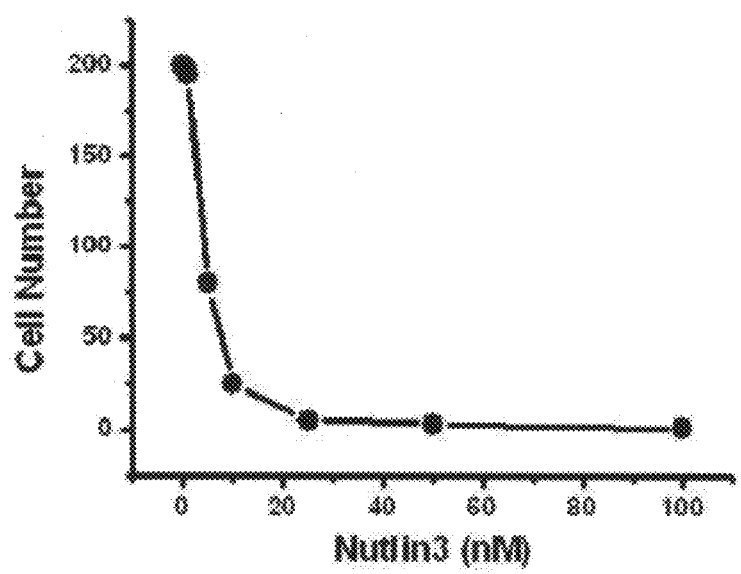
FIG. 16 shows the result of analyzing the binding inhibition concentration of the anticancer drug nutlin3. In order to determine the optimum concentration of the anticancer drug nutlin3, the binding inhibition effect of which was confirmed in FIG. 15, the binding inhibition effect was analyzed at various concentrations. Nutlin3 was treated at 0, 0.5, 1, 5, 10, 25, 50, 100, 200 nM. The binding inhibition effect of nutlin3 was distinct from 5 nM. At 10 nM, the binding between the two proteins was inhibited in more than 50% of the cells. At 25 nM, binding was not observed in more than 90% of the cells. This result shows that the binding inhibition effect of a binding inhibitor such as an anticancer drug can be precisely detected even at a very low concentration of 500 nM.

FIG. 16 shows the result of analyzing the binding inhibition concentration of the anticancer drug nutlin3. In order to determine the optimum concentration of the anticancer drug nutlin3, the binding inhibition effect of which was confirmed in FIG. 15, the binding inhibition effect was analyzed at various concentrations. Nutlin3 was treated at 0, 0.5, 1, 5, 10, 25, 50, 100, 200 nM. The binding inhibition effect of nutlin3 was distinct from 5 nM. At 10 nM, the binding between the two proteins was inhibited in more than 50% of the cells. At 25 nM, binding was not observed in more than 90% of the cells. This result shows that the binding inhibition effect of a binding inhibitor such as an anticancer drug can be precisely detected even at a very low concentration of 500 nM.

Figure 17:
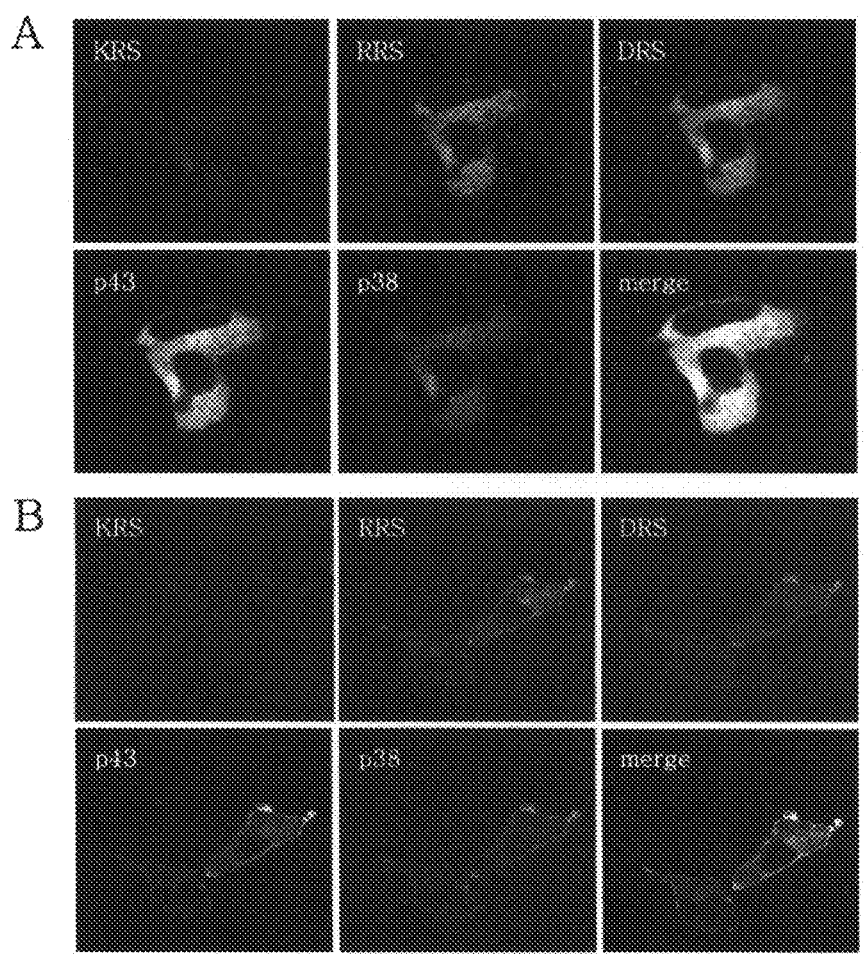
FIG. 17 shows the result of analyzing the binding of five protein complexes. In order to verify whether the binding of a plurality of proteins can be analyzed, the first construct TMD-HcR-p38 was prepared and each of second construct, BFP-KRS, CFP-RRS, GFP-DRS, YFP-p43 was prepared, respectively. The five constructs were overexpressed in HEK-293 cell line and their binding was observed using a confocal laser fluorescence microscope. Fluorescence signals (blue, cyan, green, yellow and red) reflecting the five proteins were uniformly distributed in the cytoplasm and nucleus prior to PMA treatment (A). However, after the PMA treatment (B), all of them moved toward the cell membrane. This result means that complexes composed of five proteins can be analyzed at the same time using the constructs of the present invention.

FIG. 17 shows the result of analyzing the binding of five protein complexes. In order to verify whether the binding of a plurality of proteins can be analyzed, the first construct TMD-HcR-p38 was prepared and each of second construct, BFP-KRS, CFP-RRS, GFP-DRS, YFP-p43 was prepared, respectively. The five constructs were overexpressed in HEK-293 cell line and their binding was observed using a confocal laser fluorescence microscope. Fluorescence signals (blue, cyan, green, yellow and red) reflecting the five proteins were uniformly distributed in the cytoplasm and nucleus prior to PMA treatment (A). However, after the PMA treatment (B), all of them moved toward the cell membrane. This result means that complexes composed of five proteins can be analyzed at the same time using the constructs of the present invention.

Accordingly, the present invention provides a method capable of detecting bindings and interactions occurring in a living cell in real time, and a method for screening a material that alters the interaction. The method of the present invention overcomes the disadvantages including inaccuracy and complexity of existing biomaterial interaction detection techniques, including in vitro method (in vitro and biochemical techniques), antibody binding techniques (antibody precipitation), fluorescence resonance energy transfer (FRET), bimolecular fluorescence complementation (Bi-FC) and fluorescence correlation spectroscopy (FCS) techniques, etc. By labeling both constructs to promote accuracy, the present invention provides a novel real-time, antibody-free analysis.

EXAMPLES

Hereinafter, the present invention will be described in detail referring to the examples.

However, the following examples are for illustrative purposes only and are not intended to limit the scope of the present invention.

Example 1

Animal Cell Line and Transformation

<1-1> Animal Cell Line and Culturing

CHO-k1 (ATCC CCL-61, *Cricetulus griseus*, hamster, Chinese), HEK293 (ATCC CRL-1573, *Homo sapiens*, human), HeLa (ATCC CCL-2, *Homo sapiens*, human) and SH-SY5Y (ATCC CRL-2266, *Homo sapiens*, human) cell lines were used. The animal cells were cultured according to the instructions of ATCC (American Type Culture Collection) for the individual cells. CHO-k1 cells were cultured using F-12 medium, and HEK293, HeLa and SH-SY5Y cells were cultured using DMEM medium. Other culturing condition was the same. The cells were cultured as follows (Those skilled in the art may modify the specific conditions depending on purposes.). The cells were cultured in pH 7.4 medium (F-12 and DMEM) containing 25 mM HEPES, 10% fetal bovine serum (FBS, v/v), 100 units/ml penicillin and 100 µg/ml streptomycin in a 5% $CO_2$ incubator maintained at 37° C.

<1-2> Transformation of Cell Line

In the Examples of the present invention, genes were introduced into the cells using ExGene 500 (Fermentas Life Science), one of the liposome-based techniques. All the conditions for the gene introduction including gene concentration were pursuant to the manufacturer's instructions. More specifically, after transferring the subcultured cells to a 12-well plate with a cover slip, followed by culturing for a day, the culture medium was replaced with 0.9 ml of fresh medium. About 1 µg of the transformation sample was added to 0.1 ml of 150 mM NaCl solution. After completely mixing, 3.3 µl of ExGene reagent was added and mixed by vortexing for 15 seconds. The resultant solution was allowed to stand at room temperature for 10 minutes and then added to each well of the 12-well plate in which the cells were growing. The cells were allowed to be transformed by culturing for 18 hours.

Example 2

Design and Preparation of First Construct and Second Construct

<2-1> Design and Preparation of First Construct

The first construct may be fused construct comprising a translocation module capable of moving the protein uniformly expressed in the cytoplasm toward the cell membrane, a fluorescent protein analyzable using a microscope, and a bait.

Vectors expressing the first construct (see A of FIG. 4) were prepared as follows. Translocation modules were prepared by PCR using the following templates and primers and inserted at the NheI/AgeI site of a pEGFP-C3 vector (GenBank Accession No. U57607; Clontech Catalog No. #6082-1, SEQ ID NO: 21) and a pmRFP-C3 vector (mRFP; GenBank Accession No. DQ903889, SEQ ID NO: 22), thereby completing the vectors.

The TMD translocation module was prepared by PCR using a pCMV-SPORT6-PRKCD vector [GenBank Accession No. BC043350; purchased from Open Biosystems (see the world wide web at (www)openbiosystems.com); Catalog No. EHS1001-410108-BC043350] as template and SEQ ID NO: 23 (PRKCD-F; 5'-GAAGCTAGCCGCCACCATG-GCGCCGTTCCTGC-3') and SEQ ID NO: 24 (PRKCD-R; 5'-GAAACCGGTGGATCTTCCAGGAGGT-GCTCGAATTTGG-3') as primers. And, the TMA translocation module was prepared by PCR using a pCMV-SPORT6-PRKCD vector as template and SEQ ID NO: 25 (TMA-F; 5'-GAAGCTAGCCGCCACCATGAAACAGGC-CAAAATCCACTACATC-3') and SEQ ID NO: 26 (TMA-R; 5'-GAAACCGGTGGAGTGTCCCGGCTGTTGGCCGC-3') as primers. Further, the TMB translocation module was prepared by PCR using a pCMV-SPORT6-PRKCD vector as template and SEQ ID NO: 27 (TMB-F; 5'-GCAGCTAGC-CGCCACCATGCAGAAAGAACGCTTCAACATCG-3') and SEQ ID NO: 28 (TMB-R; 5'-GCAACCGGTGGGGC-CTCAGCCAAAAGCTTCTG-3') as primers. Further, the TMB translocation module was prepared by PCR using a pCMV-SPORT6-PRKCD vector as template and SEQ ID NO: 27 (TMB-F; 5'-GCAGCTAGCCGCCACCATGCA-GAAAGAACGCTTCAACATCG-3') and SEQ ID NO: 28 (TMB-R; 5'-GCAACCGGTGGGGCCTCAGC-CAAAAGCTTCTG-3') as primers.

<2-2> Design and Preparation of Mutated First Construct

Since the translocation module included in the first construct is derived from a protein kinase, it intrinsically has the function of phosphorylation. There is a risk that cell signaling and protein interaction in the cells where the constructs are overexpressed may be inhibited or interfered by the intrinsic function of phosphorylation. Accordingly, in the present invention, mutation is induced to deprive the phosphorylation of the translocation module. In order to substitute the 311 st amino acid (tyrosine) and the 378th amino acid (lysine) of the kinase used in the present invention, which are known as very important phosphorylation sites, with phenylalanine (Y313F) and arginine, respectively, mutagenesis by PCR was performed and, finally, TMD translocation module was prepared.

To this end, genes were amplified using a forward primer (PKCD-F; 5'-GAAGCTAGCCGCCACCATGGCGCCGT-TCCTGC-3', SEQ ID NO: 29) and a modified reverse primer (Y313F-R; 5'-GAAACCCTGAAATATCCCAAC-3', SEQ ID NO: 30) under a first PCR condition, and then genes were amplified using a modified forward primer (Y313F-F; 5'-GT-TGGGATATTTCAGGGTTTC-3', SEQ ID NO: 31) and a reverse primer (PKCD-R; 5'-GAAACCGGTGGATCTTC-CAGGAGGTGCTCGAATTTGG-3', SEQ ID NO: 32) under a second PCR condition. The PCR product obtained from the first and second PCR were used as template for a third PCR using forward and reverse primers. The resultant gene is a Y313F mutant wherein the nucleotide sequence TAT is substituted by TTT. Using the gene as template, a K378R mutant wherein AAG is substituted by AGG was prepared through the same experimental procedure, using a forward primer (SEQ ID NO: 29), a reverse primer (SEQ ID NO: 32), a modified forward primer (K378R-F: 5'-TTTGCCATCA-GGGCCCTCAAG-3', SEQ ID NO: 33) and a modified reverse primer (K378R-R: 5'-CTTGAGGGCC-CTGATGGCAAA-3', SEQ ID NO: 34).

<2-3> Adhesion of NLS and NES to First Construct

Since the proteins existing in the organisms have their own distribution characteristics (targeting), the bait and prey may have targeting sites in the cell organelles. In this case, the detection of the change of the location of the first construct and second construct may be difficult. Accordingly, there is a need to control the distribution to the cytoplasm or nucleus so that the binding between the bait and prey can be verified through experiments. To this end, a vector capable of controlling the locational distribution of the bait and prey was prepared using a nuclear exclusion signal (NES) which targets a protein to the cytoplasm and a nuclear localization signal (NLS) which targets a protein to the nucleus.

The vector for locational control makes it possible to recognize whether the binding between the bait and prey occurs in the cytoplasm or in the nucleus. That is, assuming that the bait and prey bind in the cytoplasm and move toward cytoplasm, a combination of a first construct and a second construct both containing an NES allows the second construct to bind with the first construct and to move toward the cell membrane by PMA treatment, whereas a combination of constructs both containing an NLS allows only the first construct to move toward the nuclear membrane, not showing the movement of the second construct. In contrast, assuming that the bait and prey bind only in the nucleus, a combination of constructs both containing an NLS allows the constructs to move toward the nuclear membrane by PMA treatment, whereas a combination of constructs both containing an NES allows only the first construct to move toward the cell membrane, not showing the movement of the second construct.

The first construct and second construct comprising an NLS were prepared through a series of conventional PCR cloning method using the following primers. A first PCR was carried out using a pmRFP-C3 vector as template and using SEQ ID NO: 35 (NLS-F-1: 5'-AGTAAAAAGGAAAAG-GATAAATAGATAACTGATCATAATCAGCC-3') and SEQ ID NO: 36 (NLS-R: 5'-GCTGCAATAAACAAGTTAA-CAAC-3') as primers. A second PCR was carried out using the resultant PCR product as template and using SEQ ID NO: 37 (NLS-F-2: 5'-TGGAAGAAGTAGCTAAGAAGAA-GAGTAAAAAGGAAAAGGATAAA-3') and SEQ ID NO: 36 (NLS-R) as primers. Similarly, a third PCR was carried out using SEQ ID NO: 38 (NLS-F-3: 5'-TCCGGTGAT-GAAGTCGAAGGAGTGGAAGAAG-TAGCTAAGAAGAA-3') and SEQ ID NO: 36 (NLS-R) as primers, and a fourth PCR was carried out using SEQ ID NO: 39 (NLS-F-4: 5'-GCTGGATCCAGGCTCTGGTGAT-GAAGTCGAAGG-3') and SEQ ID NO: 36 (NLS-R). Thus obtained gene fragments were inserted at the BamHI/HpaI site of the first construct vector or the second construct vector.

The first construct and second construct comprising an NES were prepared in the same manner, using the following primers. A first PCR was carried out using a pmRFP-C3 vector as template and using SEQ ID NO: 40 (NES-F-1: 5'-GTGGGAAACATTTCCCTGGTGTA-GATAACTGATCATAATCAGCC-3') and SEQ ID NO: 41 (NES-R: 5'-GCTGCAATAAACAAGTTAACAAC-3') as primers. A second PCR was carried out using the resultant PCR product as template and using SEQ ID NO: 42 (NES-F-2: 5'-GTCATCATCAAGCTGAACGCCCATGTGG-GAAACATTTCCCTGGT-3') and SEQ ID NO: 41 (NES-R) as primers. Similarly, a third PCR was carried out using SEQ ID NO: 43 (NES-F-3: 5'-GTCGGATCCAGAC-CAGCGCGTCATCATCAAGCTGAACGC-3') and SEQ ID NO: 41 (NES-R) as primers. Thus obtained gene fragments were inserted at the BamHI/HpaI site of the first construct vector or the second construct vector.

<2-4> Design and Preparation of Second Construct

The second construct comprises a labeling material for analyzing the movement of the prey which has characteristic for binding with the bait of the first construct. The second construct was prepared using a fluorescent material other than used in the first construct. Using green fluorescent protein (EGFP, AzG), red fluorescent protein (mRFP) and infrared fluorescent protein (HcR), the second construct was prepared by the method described for the first construct.

When EGFP was used as the second labeling material, a pEGFP-C3 vector (Clontech) was used. When mRFP was used, a pmRFP-C3 vector was used. When AzG was used, a pAzG-C3 vector was used. And, when HcR was used, a pHcR-C3 vector was used. The C3 vectors had been prepared by substituting the EGFP gene sequence site of the pEGFP-C3 vector with AzG and HcR genes, as follows.

The pAzG-C3 vector was prepared as follows. PCR was carried out using a pPM-mAG1 vector (purchased from MBL, Catalog No. AM-V0203; Karasawa, S., et al. 2003, *J. Biol. Chem.* 278, 34167-34171) as template and using SEQ ID NO: 44 (AzG-F: 5'-GGCACCGGTCGCCACCATG-GACCCCATGGTGAGTGTGAT-3') and SEQ ID NO: 45 (AzG-R: 5'-GGCAGATCTGACAGCTTGGCCTGACTCG-GCAGCAT-3') as primers. Then, the EGFP nucleotide sequence of the pEGFP-C3 vector was substituted at the AgeI/NotI site by the resultant PCR product.

The pHcR-C3 vector was prepared as follows. PCR was carried out using pHcRed-Tandem-N1 (purchased from Avrogen, Catalog No. FP204; Gurskaya et al., 2001, *FEBS Lett.* 507, 16-20.) as template and using SEQ ID NO: 46 (HcR-F: 5'-GCCACCGGTCGCCACCATGGTGAG-3') and SEQ ID NO: 47 (HcR-R: 5'-GCCGCGGCCGCTTATCAGT-TGGCCTTCTCGGGCAGGTC-3') as primers. Then, the EGFP nucleotide sequence of the pEGFP-C3 vector was substituted at the AgeI/NotI site by the resultant PCR product.

Example 3

Verification of Translocation Characteristics of First Construct and Second Construct <3-1> Verification of Expression of Constructs and Analysis of Translocation Characteristics A cover slip containing the cells in which the first construct and second construct vectors had been introduced was fixed to a perfusion chamber and mounted on the object stage of a confocal laser fluorescence microscope (Carl Zeiss LSM510). Images of the construct vectors were taken before and after external stimulation (treatment with 1 µM PMA).

488 nm argon laser (EGFP or AzG), 543 nm HeNe laser (mRFP) or 561 nm DPSS laser (HcR) of the confocal laser fluorescence microscope was used to excite the fluorescent label, and the fluorescence signal generated by each fluorescent label was filtered through the band path filter BP505-530 (EGFP or AzG), long path filter LP560 or BP560-630 (mRFP) or long path filter LP650 (HcR). Images were taken after completely removing the interference between the fluorescences.

As a result, the green or red fluorescence emitted by the first construct vector comprising the translocation module (TMD) moved toward the cell membrane (see FIG. 5A), whereas the green or red fluorescence emitted by the second construct vector with no translocation module was uniformly distributed in the cytoplasm as before the stimulation (see FIG. 5B).

Accordingly, it can be seen that the second construct vector does not respond to the external stimulation and that the movement of the second construct toward the cell membrane necessarily requires the binding of the bait and prey.

<3-2> Verification of Translocation of First Construct and Optimum Concentration of External Stimulant Translocation efficiency of the first construct using the pTMD-mRFP-C3 vector depending on the concentration of external stimulant PMA was measured as follows. The expression vector of the first construct was transformed into CHO-k1 cells and overexpressed. After 18 hours of culturing, PMA was treated at 1, 5, 10, 20, 40, 50, 80 and 100 nM and 1 and 5 µM. 5 minutes after the PMA treatment, the cells were fixed with 3.8% formaldehyde and observed using a confocal microscope (Carl Zeiss LSM 510). 200 cells exhibiting red fluorescence were randomly selected and the distribution of the red fluorescence at the cell membrane was measured for each concentration.

As a result, as seen in FIG. 6, translocation was observed in 90% or more of the cells at 50 nM. At 100 nM or above, translocation of the red fluorescence toward the cell membrane increased. Therefore, it can be seen that treatment at a concentration of 50 nM to 5 µM is preferred, but treatment at 1 µM, which is a concentration sufficient for the response and movement of most cells, is effective.

Example 4

Analysis of Binding in Cell in Real Time Using First Construct and Second Construct <4-1> Analysis of Binding Between p53 Protein and SV40T Antigen in Cell For the binding between p53, which is known as a potential carcinogenic gene, and SV40T antigen, which is known to bind to p53, there is a commercialized binding screening system based on IP. Analysis was carried out using the same proteins in order to verify the basic binding detection ability of the present invention. In order to verify the binding between p53 and SV40T antigen in cell, a first construct in which the p53 protein is fused (TMD-mRFP-p53) and a second construct in which the SV40T antigen is fused were prepared as follows.

The first construct TMD-mRFP-p53 was prepared as follows. PCR was carried out using a pGBK-p53-GAL4 vector (p53; GenBank Accession No. AF161020) as template and using SEQ ID NO: 48 (p53-F: 5'-GAAGAATTCTGATGC-CTGTCACCGAGACCCCTGGG-3') and SEQ ID NO: 49 (p53-R: 5'-GAAGGATCCCGTCAGTCTGAGTCAGGC-CCCACTT-3') as primers. The resultant PCR product was inserted at the EcoRI/BamHI site of the pTMD-mRFP-C3 vector (a vector obtained by inserting a TMD sequence into an mRFP-C vector, see Example 2).

The second construct EGFP-SV40T was prepared as follows. PCR was carried out using a pGADT7-SV40T-GAL4 vector (SV40T; GenBank Accession No. BC014270) as template and using SEQ ID NO: 50 (SV40T-F: 5'-GAAGAAT-TCTGATGGGAACTGATGAATGGGAGCAG-3') and SEQ ID NO: 51 (SV40T-R: 5'-GAAGGATCCCGTTAT-GTTTCAGGTTCAGGGGG-3') as primers. The resultant PCR product was inserted at the EcoRI/BamHI site of the pEGFP-C3 vector.

The first construct (TMD-mRFP-p53) and the second construct (EGFP-SV40T) were introduced into CHO-k1 cells according to the procedure described in Example <1-2> (Ex-Gene 500) and allowed to be expressed. After 18 hours of culturing, followed by treatment with 1 µM PMA for 5 minutes, fluorescence distribution of the two constructs was observed as in Example <3-1>.

As seen in FIG. 10, both the red fluorescence (left panel) emitted by the bait p53 protein bound to the translocation module and the green fluorescence (central panel) emitted by the prey SV40T moved toward the cell membrane after the PMA treatment. In contrast, considering that translocation toward the cell membrane did not occur in a control group wherein only the second construct not bound to SV40T was expressed (result not shown), it can be seen that the prey SV40T binds with the bait p53 in the cell. Also, because the change of distribution of prey was appeared due to the change of distribution of bait, to which a translocation module was attached, it is confirmed that the two proteins bind to each other in cell.

<4-2> Analysis of Binding Between KRS Protein and p38 (AIMP2) Protein

Lysyl-tRNA synthetase (KRS), known as a multifunctional pathogenic gene, is known to form a complex with p38/AIMP2 protein and at least 3 other aminoacyl-tRNA synthetases (ARSB) (*J. Cell Science*, 2004, 117, 3725-3734, references therein). Accordingly, in order to verify the possibility of analyzing the binding of KRS protein and p38 protein in a cell in real time, the applicability in various animal cells, the diversity of fluorescent labels, and the exchangeability of the bait and prey, analysis was carried out using p38, which is known to bind with KRS, and using Gag and LR, which are expected as potential binding proteins.

To this end, a first construct (TMD-mRFP-p38, TMD-mRFP-Gag or TMD-mRFP-LR) and a second construct (AzG-KRS) were prepared as follows. AzG was used instead of EGFP as the fluorescence for the second construct.

The first construct TMD-mRFP-p38 was prepared as follows. PCR was carried out using a pGEX-4T1-p38 vector (p38; GenBank Accession No. NM_006303) as template and using SEQ ID NO: 52 (p38-F: 5'-GTCCTCGAGATGC-CGATGTACCAGGTAAAG-3') and SEQ ID NO: 53 (p38-R: 5'-GTCGGATCCTTAAAAAGGAGCCAGGTTTTC-3') as primers. The resultant PCR product was inserted at the XhoI/BamHI site of the pTMD-mRFP-C3 vector.

TMD-mRFP-Gag was prepared as follows. PCR was carried out using a pGEX-4T1-Gag vector (Gag; GenBank Accession No. NM_002295) as template and using SEQ ID NO: 54 (Gag-F: 5'-GTCGAATTCTGATGGGTGC-GAGAGCGTCAGTA-3') and SEQ ID NO: 55 (Gag-R: 5'-GTCGGATCCTTATTGTGACGAGGGGTCGTT-3') as primers. The resultant PCR product was inserted at the XhoI/BamHI site of the pTMD-mRFP-C3 vector.

TMD-mRFP-LR was prepared as follows. PCR was carried out using a pET28a-TEV-LR vector (LR; GenBank Accession No. NM_002295) as template and using SEQ ID NO: 56 (LR-F: 5'-GTCGAATTCTGATGTCCGGAGCCCT-TGATGT-3') and SEQ ID NO: 57 (LR-R: 5'-GTCGGATC-CTTAAGACCAGTCAGTGGTTGCTC-3') as primers. The resultant PCR product was inserted at the XhoI/BamHI site of the pTMD-mRFP-C3 vector.

The second construct AzG-KRS was prepared as follows. PCR was carried out using pET28a (GenBank Accession No. NM_005548) as template and using SEQ ID NO: 58 (KRS-F: 5'-GTCGAATTCTGATGGCGGCCGTGCAGGCG-3') and SEQ ID NO: 59 (KRS-R: 5'-GTCCCCGGGCTAGACA-GAAGTGCCAACTGTTGTG-3') as primers. The resultant PCR product was inserted at the EcoRI/BamHII site of the pAzG-C3 vector.

Thus prepared first construct and second construct were transformed into HEK293 cell line. Fluorescence was observed as in the same manner as in Example <4-1> except for using DMEM.

As seen in FIG. 11, all the three proteins of the first construct were observed to move toward the cell membrane (left panel). As for p38 (see FIG. 11 A), which is known to bind to KRS, the second construct bound to KRS moved toward the cell membrane. However, such translocation was not observed for the potential binding proteins Gag (see FIG. 11 B) and LR (see FIG. 11 C) (central panel). Accordingly, it was verified that KRS protein binds with p38 protein but not with Gag or LR protein. Further, it was verified that AzG fluorescent protein may be used instead of EGFP.

<4-3> Analysis of Binding Between RelA Protein and Inhibitor Protein IkB in Cell in Real Time It is known that the interactions of NFkB and IkB proteins regulated by TNF-alpha are involved with various cell signaling pathways occurring in cells. Of the various cell signaling pathways, particularly noticeable is the close relationship with inflammatory responses against various harmful signals in body. Accordingly, in order to verify the binding of the multifunctional inflammation-related gene RelA and the inhibitor protein IkB, among the NFkB complexes, and to demonstrate the possibility of direct analysis in living cells after external stimulation, not by cell fixation, experiments were carried out using a real-time (time-laps) technique.

To this end, a first construct (TMD-mRFP-RelA) and a second construct (EGFP-IkB) were prepared as follows.

The first construct TMD-mRFP-RelA was prepared as follows. PCR was carried out using a pEYFP-RelA vector (RelA; GenBank Accession No. NM_021975) as template and using SEQ ID NO: 60 (RelA-F: 5'-GGACTCGAGATG-GACGAACTGTTCCCCCTC-3') and SEQ ID NO: 61 (RelA-R: 5'-GAAGGATCCCGTTAGGAGCTGATCT-GACTCAGCAGG-3') as primers. The resultant PCR product was inserted at the XhoI/BamHI site of the pTMD-mRFP-C3 vector.

The second construct EGFP-IkB was prepared as follows. PCR was carried out using a pcDNA3-IkB vector (IkB; GenBank Accession No. NM_020529) as template and using SEQ ID NO: 62 (IkB-F: 5'-GAAGAATTCTGATGTTC-CAGGCGGCCGAGCG-3') and SEQ ID NO: 63 (ikB-R: 5'-GAAGGATCCCGTCATAAACGTCA-GACGCTGGCCTCCAA-3') as primers. The resultant PCR product was inserted at the EcoRI/BamHI site of the pEGFP-C3 vector.

Thus prepared first construct and second construct were transformed into CHO-k1 cell line and fluorescence was observed as in Example <4-1> at 0, 1, 2 and 3 minute.

As seen in FIG. 12, the first construct (TMD-mRFP-RelA) was uniformly distributed in the cell at 0 minute, but moved gradually toward the cell membrane with the lapse of time (left panel). The second construct (EGFP-IkB) was also uniformly distributed in the cell at 0 minute, but moved gradually toward the cell membrane along with the first construct with the lapse of time (central panel). Especially, the constructs were observed to move toward the cell membrane from at about 10 seconds after the PMA treatment (not shown in the figure). The translocation was completed in most cells within 3 minutes. This tendency was observed similarly in all the preceding examples and all the following examples (not shown in the figure).

<4-4> Analysis of Binding of Multifunctional Inflammation-Related Gene NFkB Complex (RelA/p50/IkB) in Cell Basically, the NFkB complex is known to be formed by NFkB (RelA/p50) and the negative regulator IkB protein. It was verified whether the binding of the three proteins RelA, p50 and IkB, which constitute the complex, can be identified.

To this end, a first construct (TMD-mRFP-RelA) and two second constructs (EGFP-IkB and HcR-p50) were prepared as follows. As the fluorescent label, mRFP was used for the first construct, and EGFP and HcR (HcRed), which is distinguishable to mRFP, were used for the second constructs.

The first construct (TMD-mRFP-RelA) and the IkB-comprising second construct (EGFP-IkB) were the same as those used in Example <4-3>. The other second construct HcR-p50 was prepared as follows. PCR was carried out using a pDMV-SPORT6-NFkB1 vector (NFkB1; GenBank Accession No. BC006231) as template and using SEQ ID NO: 64 (p50-F: 5'-GCTGAATTCTGATGGCAGAAGATGATCCATATT-3') and SEQ ID NO: 65 (p50-R: 5'-GCTCCCGGGCTTAAT-GCTTCATCCCAGCATTAGA-3') as primers. The resultant PCR product was inserted at the EcoRI/XmaI site of the pHcR-C3 vector.

Thus prepared first construct and two second constructs were transformed into HEK293 cell line, and fluorescence was observed as in Example <4-1>.

As seen in FIG. 13, all the first construct (TMD-mRFP-RelA, red), the second construct (EGFP-IkB, green) and the second construct (HcR-p50, blue) moved toward the cell membrane in response to the PMA stimulation. In contrast, the change of distribution was not observed in the control group (TMD-mRFP) wherein the first construct did not include a translocation module (not shown in the figure).

This experimental result indicates that not only the binding of the three protein complexes comprising the first construct, but also the binding of four complexes EGFP, mRFP, HcRed and BFP with the fluorescent label removed from the first construct can be verified using a generally used fluorescence microscope or confocal laser fluorescence microscope. Using various fluorescent protein species and the Meta (Carl Zeiss) or Spetral (Leica) fluorescence microscope, at least five protein complexes including BFP, CFP, GFP, RFP and Far-Red can be detected in addition to the first construct.

<4-5> Analysis of Binding of Multiple Interactions of Proteins (Lysyl RNA Synthetase (KRS), Arginyl RNA Synthetase (RRS), Asparagyl RNA Synthethase (DRS), p43 and p38)

In order to examine whether the method of the present invention could validate the complex binding of multiple proteins, p38 was inserted in the $1^{st}$ construct attached a translocation module and each of KRS, RRS, DRS and p43 was inserted in the $2^{nd}$ constructs, respectively. Thus prepared first construct and two second constructs were transformed into HEK293 cell line, and fluorescence was observed as in Example <4-1>.

As can be seen in FIG. 17, the inventors found that PMA treatments make fluorescence dye of RRS, DRS, p43 and p38 as well as KRS to move to a cell membrane, thereby binding to the inside of the cell.

Example 5

Verification of Candidate Materials Screened Through Y2H

Currently, Y2H is the most widely used for screening protein bindings in a living cell. It is also the typical method used for new drug screening. However, Y2H is disadvantageous in new drug targeting and verification because of the high false positive and the use of yeast. Accordingly, the applicability of the present invention as a method of verifying the candidate materials screened through Y2H was investigated.

Four positive clones were screened through Y2H for super bacteria (antibiotics-resistant bacteria)-related OmpA (GenBank Accession No. AY485227) protein and human protein library (Entire library screening clones: $1.188 \times 10^5$ clones; first patch/streak screening: 137 clones; second re-transformation screening: 54 clones; third prey auto-activation test screening: 14 clones; fourth nucleotide sequencing confirmation: 4 clones).

Among the four positive clones, EEF1A1 (GenBank Accession No. BC009875), FAM14B (GenBank Accession No. BC015423) and DDX31 (GenBank Accession No. AK027002) were tested for binding with the OmpA protein. To this end, a first construct (TMD-mRFP-OmpA) and second constructs (EGFP-EEF1A, EGFP-FAM14B and EGFP-DDX31) were prepared as follows.

The first construct TMD-mRFP-OmpA was prepared as follows. PCR was carried out using a pET28a-OmpA (GenBank Accession No.: AY185227) vector as template and using SEQ ID NO: 66 (OmpA-F: 5'-GCTGAATTCTGAT-GAAATTGAGTCGTATTGCAC-3') and SEQ ID NO: 67 (OmpA-R: 5'-GCTGGATCCTTATTGAGCTGCTGCAG-GAGC-3') as primers. The resultant PCR product was inserted at the EcoRI/BamHI site of the pTMD-mRFP-C3 vector.

The second constructs were prepared as follows. For EGFP-EEF1A, a pOTB7-EEF1A (GenBank Accession No. BC009875) vector was used as template and SEQ ID NO: 68 (EEF1A-F: 5'-GCTGAATTCTGATGGGAAAGGAAAA-GACTCA-3') and SEQ ID NO: 69 (EEF1A-R: 5'-GCTG-GATCCCGCTATTTAGCCTTCTGAGCTT-3') were used as primers. For EGFP-FAM14B, a pCMV-SPORT6-FAM14B (GenBank Accession No.: BC015423) vector was used as template and SEQ ID NO: 70 (FAM14B-F: 5'-GTCGAAT-TCTGATGGGAAAGGAGAGTGGATGG-3') and SEQ ID NO: 71 (FAM14B-R: 5'-GTCGGATCCCGTCAGCTG-GAAGGGGGTGAAC-3') were used as primers. For EGFP-DDX31, a pME18S-FL3-DDX31 vector was used as template and SEQ ID NO: 72 (DDX31-F: 5'-GTCGAATTCTGATGTTTCTCCAAAGAAGCAT-3') and SEQ ID NO: 73 (DDX31-R: 5'-GTCGGATCCCGT-TAAACTTTCTGGGAAGTCTTG-3') were used as primers. After carrying out PCR, each PCR product was inserted at the EcoRI/BamHI site of the pEGFP-C3 vector.

Thus prepared first construct and second constructs were transformed into HEK293 cell line, and fluorescence was observed as in Example <4-1>.

As seen in FIG. 14, EEF1A1 (A) and FAM14B (B) did not move toward the cell membrane along with the OmpA-bound first construct (false positive). In contrast, DDX31 (C) moved toward the cell membrane along with the OmpA-bound first construct, and thus, was confirmed as positive. Therefore, it can be seen that the method of the present invention provides better accuracy than Y2H and enables reconfirmation of positive binding.

Example 6

Verification of Efficiency of Anticancer Drug Through Real-Time Analysis p53 protein, known as a potential carcinogenic protein, is known to facilitate carcinogenesis by binding at least to mdm2 protein. Through researches, nutlin3 was confirmed as a potent anticancer drug capable of inhibiting it. In an in vitro binding inhibition experiment using Biacore's surface plasmon resonance (SPR) technology, a p53-mdm2 binding inhibition effect of 90% or more was attained when at least 1 micromolar of nutlin3 was treated, and the median inhibitory concentration (IC50) was about 90 nanomolar (Vassilev, L. T. et. al., 2004, *Science* 303, 844-848).

The interaction between p53 (GenBank Accession No. NM_00546) and mdm2 and the binding inhibition by nutlin3 were verified in living human cell line. To this end, a first construct (TMD-mRFP-p53N) and a second construct (AzG-mdm2N) were prepared as follows.

The first construct TMD-mRFP-p53N was prepared as follows. PCR was carried out using a pGEX-4T1-p53N vector (p53; GenBank Accession No. NM_000546) as template and using SEQ ID NO: 74 (p53N-F: 5'-GTCGAATTCTCATG-GAGGAGCCGCAGTCAGAT-3') and SEQ ID NO: 75 (p53N-R: 5'-GTCGGATCCTCACACGGGGGGAG-CAGCCT-3') as primers. The resultant PCR product was inserted at the EcoRI/BamHI site of the first construct vector (pTMD-mRFP-C3 vector).

The second construct EGFP-mdm2N was prepared as follows. PCR was carried out using a pGEX-4T1-mdm2N vector (mdm2; GenBank Accession No. NM_002392) as template and using SEQ ID NO: 76 (mdm2N-F: 5'-GTCGAATTCTGATGTGCAATACCAACAT-GTCTGTACC-3') and SEQ ID NO: 77 (mdm2N-R: 5'-GTCGGATCCTCATACTACCAAGTTCCTGTAGAT-3') as primers. The resultant PCR product was inserted at the EcoRI/BamHI site of the pAzG-C3 vector.

Thus prepared first construct and second construct were transformed into HEK393 cell line, and fluorescence was observed as in Example <4-1>. Nutlin3 was treated at 0, 0.5, 1, 5, 10, 25, 50, 100 and 200 nM. As in Example <3-2>, after treating with nutlin3 for 5 minutes, the cells were fixed with 3.8% formaldehyde and observed using a confocal microscope (Carl Zeiss LSM 510). 200 cells exhibiting red fluorescence were randomly selected and the distribution of the red fluorescence at the cell membrane was measured for each concentration.

As seen in FIG. 15, mdm2 (green, central panel) moved toward the cell membrane in a living cell along with p53 (red, left panel) in response to the external stimulation (PMA) (see FIG. 15 A), whereas a change in distribution was not observed when the inhibitor nutlin3 was treated (see FIG. 15 B). This indicates that mdm2 binds with p53 in the absence of nutlin3, but the binding of mdm2 and p53 is inhibited by nutlin3. This result shows that the present invention enables a direct analysis of protein interactions occurring in a living cell and may be useful as a tool for new drug development associated with the bindings.

Also, as seen in FIG. 16, by the result that 200 cells exhibiting red fluorescence were randomly selected and the distribution of the red fluorescence at the cell membrane was measured for each concentration, a binding inhibition effect of 95% or more was attained at 20 nanomolar (nM), whereas a binding inhibition effect of 90% or more was attained at 1 micromolar in an in vitro experiment for living human cells (HEK293) using recombinant proteins (Vassilev, L. T. et. al., 2004, *Science* 303, 844-848). Accordingly, it can be seen that the present invention provides an analysis accuracy of about 50 times that of the existing in vitro technique. In addition, this result indicates that the present invention provides a technique capable of avoiding the risk of research for cells or body and clinical tests for humans, by the in vitro inhibitory result.

As described, the present invention provides a method enabling real-time detection of bindings and interactions of materials occurring in a living cell and a method for screening a material altering such interactions. The method of the present invention overcomes the disadvantages including inaccuracy and complexity of existing biomaterial interaction detection techniques, including in vitro method (in vitro and biochemical techniques), antibody binding (antibody precipitation) techniques, FRET, Bi-FC and FCS techniques, etc. By labeling both constructs to promote accuracy, the present invention provides a novel real-time, antibody-free analysis.

The invention claimed is:

1. A method for detecting interactions of a bait and a prey comprising the steps of:
   (a) preparing a cell comprising
      (i) a first construct comprising a bait, a first labeling material and a translocation module; and
      (ii) a second construct comprising a prey and a second labeling material;
   (b) allowing the bait of the first construct and the prey of the second construct to interact;
   (c) treating with a signaling material to translocate the first construct to the plasma membrane of the cell; and
   (d) detecting the translocation of the first construct and the second construct to the plasma membrane of the cell in the cell, wherein the translocation module is protein kinase C or its variants, wherein protein kinase C or its variants comprise an amino acid sequence selected from the group consisting of SEQ ID NO:1, SEQ ID NO:3, SEQ ID NO:5 and SEQ ID NO:7.

2. The method of claim 1, wherein the first labeling material is selected from the group consisting of GFP (Green Fluorescent Protein); EGFP (Enhanced Green Fluorescent Protein); RFP (Red Fluorescent Protein); mRFP (Monomeric Red Fluorescent Protein); DsRed (*Discosoma* sp. red fluorescent protein); CFP (Cyan Fluorescent Protein); CGFP (Cyan Green Fluorescent Protein); YFP (Yellow Fluorescent Protein); AzG (Azami Green), HcR (HcRed, *Heteractis crispa* red fluorescent protein), and BFP (Blue Fluorescent Protein).

3. The method of claim 1, wherein the second labeling material is selected from the group consisting of GFP (Green Fluorescent Protein); EGFP (Enhanced Green Fluorescent Protein); RFP (Red Fluorescent Protein); mRFP (Monomeric Red Fluorescent Protein); DsRed (*Discosoma* sp. red fluorescent protein); CFP (Cyan Fluorescent Protein); CGFP (Cyan Green Fluorescent Protein); YFP (Yellow Fluorescent Protein); AzG (Azami Green), HcR (HcRed, *Heteractis crispa* red fluorescent protein), and BFP (Blue Fluorescent Protein).

4. A method for detecting interactions of a bait and a prey comprising the steps of:
   (a) preparing a cell comprising (i) a first construct comprising a bait, a first labeling material which is EGFP (Enhanced Green Fluorescent Protein) or mRFP (Monomeric Red Fluorescent Protein) and a translocation module having amino acid sequences of any one which is selected from the group consisting of SEQ ID NO: 1, SEQ ID NO:3, SEQ ID NO:5 and SEQ ID NO:7; and (ii) a second construct comprising a prey and a second labeling material of any one which is selected from the group consisting of EGFP (Enhanced Green Fluorescent Protein), mRFP (Monomeric Red Fluorescent Protein), AzG (Azami Green) and HcR (HcRed, Heteractis *crispa* red fluorescent protein);
   (b) allowing the bait of the first construct and the prey of the second construct to interact;
   (c) treating with a signaling material to translocate the first construct to the plasma membrane of the cell; and
   (d) detecting the translocation of the first construct and the second construct to the plasma membrane of the cell in the cell.

5. The method of claim 4, wherein the treatment with a signaling material is the treatment with 50 nM to 5 μM of PMA (Phorbol 12-myristate 13-acetate, Phorbol ester).

* * * * *

SEQUENCE LISTING

<160> NUMBER OF SEQ ID NOS: 77

<210> SEQ ID NO 1
<211> LENGTH: 676
<212> TYPE: PRT
<213> ORGANISM: Homo sapiens

<400> SEQUENCE: 1

```
Met Ala Pro Phe Leu Arg Ile Ala Phe Asn Ser Tyr Glu Leu Gly Ser
1               5                   10                  15

Leu Gln Ala Glu Asp Glu Ala Asn Gln Pro Phe Cys Ala Val Lys Met
            20                  25                  30

Lys Glu Ala Leu Ser Thr Glu Arg Gly Lys Thr Leu Val Gln Lys Lys
        35                  40                  45

Pro Thr Met Tyr Pro Glu Trp Lys Ser Thr Phe Asp Ala His Ile Tyr
    50                  55                  60

Glu Gly Arg Val Ile Gln Ile Val Leu Met Arg Ala Ala Glu Glu Pro
65                  70                  75                  80

Val Ser Glu Val Thr Val Gly Val Ser Val Leu Ala Glu Arg Cys Lys
                85                  90                  95

Lys Asn Asn Gly Lys Ala Glu Phe Trp Leu Asp Leu Gln Pro Gln Ala
            100                 105                 110

Lys Val Leu Met Ser Val Gln Tyr Phe Leu Glu Asp Val Asp Cys Lys
```

-continued

```
            115                 120                 125
Gln Ser Met Arg Ser Glu Asp Glu Ala Lys Phe Pro Thr Met Asn Arg
        130                 135                 140
Arg Gly Ala Ile Lys Gln Ala Lys Ile His Tyr Ile Lys Asn His Glu
145                 150                 155                 160
Phe Ile Ala Thr Phe Gly Gln Pro Thr Phe Cys Ser Val Cys Lys
                165                 170                 175
Asp Phe Val Trp Gly Leu Asn Lys Gln Gly Tyr Lys Cys Arg Gln Cys
                180                 185                 190
Asn Ala Ala Ile His Lys Lys Cys Ile Asp Lys Ile Gly Arg Cys
                195                 200                 205
Thr Gly Thr Ala Ala Asn Ser Arg Asp Thr Ile Phe Gln Lys Glu Arg
        210                 215                 220
Phe Asn Ile Asp Met Pro His Arg Phe Lys Val His Asn Tyr Met Ser
225                 230                 235                 240
Pro Thr Phe Cys Asp His Cys Gly Ser Leu Leu Trp Gly Leu Val Lys
                245                 250                 255
Gln Gly Leu Lys Cys Glu Asp Cys Gly Met Asn Val His His Lys Cys
                260                 265                 270
Arg Glu Lys Val Ala Asn Leu Cys Gly Ile Asn Gln Lys Leu Leu Ala
                275                 280                 285
Glu Ala Leu Asn Gln Val Thr Gln Arg Ala Ser Arg Arg Ser Asp Ser
        290                 295                 300
Ala Ser Ser Glu Pro Val Gly Ile Tyr Gln Gly Phe Glu Lys Lys Thr
305                 310                 315                 320
Gly Val Ala Gly Glu Asp Met Gln Asp Asn Ser Gly Thr Tyr Gly Lys
                325                 330                 335
Ile Trp Glu Gly Ser Ser Lys Cys Asn Ile Asn Asn Phe Ile Phe His
                340                 345                 350
Lys Val Leu Gly Lys Gly Ser Phe Gly Lys Val Leu Leu Gly Glu Leu
                355                 360                 365
Lys Gly Arg Gly Glu Tyr Phe Ala Ile Lys Ala Leu Lys Lys Asp Val
        370                 375                 380
Val Leu Ile Asp Asp Asp Val Glu Cys Thr Met Val Glu Lys Arg Val
385                 390                 395                 400
Leu Thr Leu Ala Ala Glu Asn Pro Phe Leu Thr His Leu Ile Cys Thr
                405                 410                 415
Phe Gln Thr Lys Asp His Leu Phe Phe Val Met Glu Phe Leu Asn Gly
                420                 425                 430
Gly Asp Leu Met Tyr His Ile Gln Asp Lys Gly Arg Phe Glu Leu Tyr
                435                 440                 445
Arg Ala Thr Phe Tyr Ala Ala Glu Ile Met Cys Gly Leu Gln Phe Leu
        450                 455                 460
His Ser Lys Gly Ile Ile Tyr Arg Asp Leu Lys Leu Asp Asn Val Leu
465                 470                 475                 480
Leu Asp Arg Asp Gly His Ile Lys Ile Ala Asp Phe Gly Met Cys Lys
                485                 490                 495
Glu Asn Ile Phe Gly Glu Ser Arg Ala Ser Thr Phe Cys Gly Thr Pro
                500                 505                 510
Asp Tyr Ile Ala Pro Glu Ile Leu Gln Gly Leu Lys Tyr Thr Phe Ser
                515                 520                 525
Val Asp Trp Trp Ser Phe Gly Val Leu Leu Tyr Glu Met Leu Ile Gly
                530                 535                 540
```

```
Gln Ser Pro Phe His Gly Asp Asp Glu Asp Glu Leu Phe Glu Ser Ile
545                 550                 555                 560

Arg Val Asp Thr Pro His Tyr Pro Arg Trp Ile Thr Lys Glu Ser Lys
            565                 570                 575

Asp Ile Leu Glu Lys Leu Phe Glu Arg Glu Pro Thr Lys Arg Leu Gly
            580                 585                 590

Val Thr Gly Asn Ile Lys Ile His Pro Phe Phe Lys Thr Ile Asn Trp
        595                 600                 605

Thr Leu Leu Glu Lys Arg Arg Leu Glu Pro Pro Phe Arg Pro Lys Val
    610                 615                 620

Lys Ser Pro Arg Asp Tyr Ser Asn Phe Asp Gln Glu Phe Leu Asn Glu
625                 630                 635                 640

Lys Ala Arg Leu Ser Tyr Ser Asp Lys Asn Leu Ile Asp Ser Met Asp
                645                 650                 655

Gln Ser Ala Phe Ala Gly Phe Ser Phe Val Asn Pro Lys Phe Glu His
            660                 665                 670

Leu Leu Glu Asp
        675

<210> SEQ ID NO 2
<211> LENGTH: 2028
<212> TYPE: DNA
<213> ORGANISM: Homo sapiens

<400> SEQUENCE: 2
atggcgccgt tcctgcgcat cgccttcaac tcctatgagc tgggctccct gcaggccgag      60
gacgaggcga accagccctt ctgtgccgtg aagatgaagg aggcgctcag cacagagcgt     120
gggaaaacac tggtgcagaa gaagccgacc atgtatcctg agtggaagtc gacgttcgac     180
gcccacatct atgaggggcg cgtcatccag attgtgctaa tgcgggcagc agaggagcca     240
gtgtctgagg tgaccgtggg tgtgtcggtc ctggccgagc gctgcaagaa gaacaatggc     300
aaggctgagt tctggctgga cctgcagcct caggccaagg tgttgatgtc tgttcagtat     360
ttcctggagg acgtggattg caaacagtct atgcgcagtg aggacgaggc caagttccca     420
acgatgaacc gccgcggagc catcaaacag gccaaaatcc actacatcaa gaaccatgag     480
tttatcgcca cctctcttgg gcaacccacc ttctgttctg tgtgcaaaga ctttgtctgg     540
ggcctcaaca agcaaggcta caaatgcagg caatgtaacg ctgccatcca agaaatgc       600 atcgacaaga tcatcggcag atgcactggc accgcggcca acagccggga cactatattc     660
cagaaagaac gcttcaacat cgacatgccg caccgcttca aggttcacaa ctacatgagc     720
cccaccttct gtgaccactg cggcagcctg ctctggggac tggtgaagca gggattaaag     780
tgtgaagact gcggcatgaa tgtgcaccat aaatgccggg agaaggtggc caacctctgc     840
ggcatcaacc agaagctttt ggctgaggcc ttgaaccaag tcacccagag agcctcccgg     900
agatcagact cagcctcctc agagcctgtt gggatatatc agggtttcga gaagaagacc     960
ggagttgctg gggaggacat gcaagacaac agtgggacct acggcaagat ctgggagggc    1020
agcagcaagt gcaacatcaa caacttcatc ttccacaagg tcctgggcaa aggcagcttc    1080
gggaaggtgc tgcttggaga gctgaagggc agaggagagt actttgccat caaggccctc    1140
aagaaggatg tggtcctgat cgacgacgac gtggagtgca ccatggttga agagcgggtg    1200 ctgcacttg ccgcagagaa tcccttctc acccacctca tctgcacctt ccagaccaag    1260
gaccacctgt tctttgtgat ggagttcctc aacgggggga acctgatgta ccacatccag    1320
```

```
gacaaaggcc gctttgaact ctaccgtgcc acgttttatg ccgctgagat aatgtgtgga    1380
ctgcagtttc tacacagcaa gggcatcatt tacagggacc tcaaactgga caatgtgctg    1440
ttggaccggg atggccacat caagattgcc gactttggga tgtgcaaaga gaacatattc    1500
ggggagagcc gggccagcac cttctgcggc acccctgact atatcgcccc tgagatccta    1560
cagggcctga agtacacatt ctctgtggac tggtggtctt tcggggtcct tctgtacgag    1620
atgctcattg gccagtcccc cttccatggt gatgatgagg atgaactctt cgagtccatc    1680
cgtgtggaca cgccacatta tccccgctgg atcaccaagg agtccaagga catcctggag    1740
aagctctttg aaagggaacc aaccaagagg ctgggagtga cgggaaacat caaaatccac    1800
cccttcttca agaccataaa ctggactctg ctggaaaagc ggaggttgga gccacccttc    1860
aggcccaaag tgaagtcacc cagagactac agtaactttg accaggagtt cctgaacgag    1920
aaggcgcgcc tctcctacag cgacaagaac ctcatcgact ccatggacca gtctgcattc    1980
gctggcttct cctttgtgaa ccccaaattc gagcacctcc tggaagat              2028

<210> SEQ ID NO 3
<211> LENGTH: 71
<212> TYPE: PRT
<213> ORGANISM: Artificial Sequence
<220> FEATURE:
<223> OTHER INFORMATION: Human Protein kinase C mutant, TMA

<400> SEQUENCE: 3

Met Lys Gln Ala Lys Ile His Tyr Ile Lys Asn His Glu Phe Ile Ala
1               5                   10                  15

Thr Phe Phe Gly Gln Pro Thr Phe Cys Ser Val Cys Lys Asp Phe Val
            20                  25                  30

Trp Gly Leu Asn Lys Gln Gly Tyr Lys Cys Arg Gln Cys Asn Ala Ala
        35                  40                  45

Ile His Lys Lys Cys Ile Asp Lys Ile Ile Gly Arg Cys Thr Gly Thr
    50                  55                  60

Ala Ala Asn Ser Arg Asp Thr
65                  70

<210> SEQ ID NO 4
<211> LENGTH: 213
<212> TYPE: DNA
<213> ORGANISM: Artificial Sequence
<220> FEATURE:
<223> OTHER INFORMATION: Human Protein kinase C mutant, TMA

<400> SEQUENCE: 4
atgaaacagg ccaaaatcca ctacatcaag aaccatgagt ttatcgccac cttctttggg     60
caacccacct tctgttctgt gtgcaaagac tttgtctggg gcctcaacaa gcaaggctac    120
aaatgcaggc aatgtaacgc tgccatccac aagaaatgca tcgacaagat catcggcaga    180
tgcactggca ccgcggccaa cagccgggac act                                  213

<210> SEQ ID NO 5
<211> LENGTH: 71
<212> TYPE: PRT
<213> ORGANISM: Artificial Sequence
<220> FEATURE:
<223> OTHER INFORMATION: Human Protein kinase C mutant, TMB

<400> SEQUENCE: 5

Met Gln Lys Glu Arg Phe Asn Ile Asp Met Pro His Arg Phe Lys Val
```

```
1               5                   10                  15
His Asn Tyr Met Ser Pro Thr Phe Cys Asp His Cys Gly Ser Leu Leu
            20                  25                  30

Trp Gly Leu Val Lys Gln Gly Leu Lys Cys Glu Asp Cys Gly Met Asn
            35                  40                  45

Val His His Lys Cys Arg Glu Lys Val Ala Asn Leu Cys Gly Ile Asn
 50                  55                  60

Gln Lys Leu Leu Ala Glu Ala
 65                  70

<210> SEQ ID NO 6
<211> LENGTH: 213
<212> TYPE: DNA
<213> ORGANISM: Artificial Sequence
<220> FEATURE:
<223> OTHER INFORMATION: Human Protein kinase C mutant, TMB

<400> SEQUENCE: 6
atgcagaaag aacgcttcaa catcgacatg ccgcaccgct tcaaggttca caactacatg      60
agccccacct tctgtgacca ctgcggcagc ctgctctggg gactggtgaa gcagggatta     120
aagtgtgaag actgcggcat gaatgtgcac cataaatgcc gggagaaggt ggccaacctc     180
tgcggcatca accagaagct tttggctgag gcc                                  213

<210> SEQ ID NO 7
<211> LENGTH: 676
<212> TYPE: PRT
<213> ORGANISM: Artificial Sequence
<220> FEATURE:
<223> OTHER INFORMATION: Human Protein kinase C mutant, TMD

<400> SEQUENCE: 7

Met Ala Pro Phe Leu Arg Ile Ala Phe Asn Ser Tyr Glu Leu Gly Ser
 1               5                  10                  15

Leu Gln Ala Glu Asp Glu Ala Asn Gln Pro Phe Cys Ala Val Lys Met
            20                  25                  30

Lys Glu Ala Leu Ser Thr Glu Arg Gly Lys Thr Leu Val Gln Lys Lys
        35                  40                  45

Pro Thr Met Tyr Pro Glu Trp Lys Ser Thr Phe Asp Ala His Ile Tyr
 50                  55                  60

Glu Gly Arg Val Ile Gln Ile Val Leu Met Arg Ala Ala Glu Glu Pro
 65                  70                  75                  80

Val Ser Glu Val Thr Val Gly Val Ser Val Leu Ala Glu Arg Cys Lys
            85                  90                  95

Lys Asn Asn Gly Lys Ala Glu Phe Trp Leu Asp Leu Gln Pro Gln Ala
            100                 105                 110

Lys Val Leu Met Ser Val Gln Tyr Phe Leu Glu Asp Val Asp Cys Lys
        115                 120                 125

Gln Ser Met Arg Ser Glu Asp Glu Ala Lys Phe Pro Thr Met Asn Arg
    130                 135                 140

Arg Gly Ala Ile Lys Gln Ala Lys Ile His Tyr Ile Lys Asn His Glu
145                 150                 155                 160

Phe Ile Ala Thr Phe Phe Gly Gln Pro Thr Phe Cys Ser Val Cys Lys
                165                 170                 175

Asp Phe Val Trp Gly Leu Asn Lys Gln Gly Tyr Lys Cys Arg Gln Cys
            180                 185                 190

Asn Ala Ala Ile His Lys Lys Cys Ile Asp Lys Ile Ile Gly Arg Cys
```

```
                       195                 200                 205
Thr Gly Thr Ala Ala Asn Ser Arg Asp Thr Ile Phe Gln Lys Glu Arg
    210                 215                 220

Phe Asn Ile Asp Met Pro His Arg Phe Lys Val His Asn Tyr Met Ser
225                 230                 235                 240

Pro Thr Phe Cys Asp His Cys Gly Ser Leu Leu Trp Gly Leu Val Lys
                245                 250                 255

Gln Gly Leu Lys Cys Glu Asp Cys Gly Met Asn Val His His Lys Cys
            260                 265                 270

Arg Glu Lys Val Ala Asn Leu Cys Gly Ile Asn Gln Lys Leu Leu Ala
        275                 280                 285

Glu Ala Leu Asn Gln Val Thr Gln Arg Ala Ser Arg Arg Ser Asp Ser
    290                 295                 300

Ala Ser Ser Glu Pro Val Gly Ile Phe Gln Gly Phe Glu Lys Lys Thr
305                 310                 315                 320

Gly Val Ala Gly Glu Asp Met Gln Asp Asn Ser Gly Thr Tyr Gly Lys
                325                 330                 335

Ile Trp Glu Gly Ser Ser Lys Cys Asn Ile Asn Asn Phe Ile Phe His
            340                 345                 350

Lys Val Leu Gly Lys Gly Ser Phe Gly Lys Val Leu Leu Gly Glu Leu
        355                 360                 365

Lys Gly Arg Gly Glu Tyr Phe Ala Ile Arg Ala Leu Lys Lys Asp Val
    370                 375                 380

Val Leu Ile Asp Asp Asp Val Glu Cys Thr Met Val Glu Lys Arg Val
385                 390                 395                 400

Leu Thr Leu Ala Ala Glu Asn Pro Phe Leu Thr His Leu Ile Cys Thr
                405                 410                 415

Phe Gln Thr Lys Asp His Leu Phe Phe Val Met Glu Phe Leu Asn Gly
            420                 425                 430

Gly Asp Leu Met Tyr His Ile Gln Asp Lys Gly Arg Phe Glu Leu Tyr
        435                 440                 445

Arg Ala Thr Phe Tyr Ala Ala Glu Ile Met Cys Gly Leu Gln Phe Leu
    450                 455                 460

His Ser Lys Gly Ile Ile Tyr Arg Asp Leu Lys Leu Asp Asn Val Leu
465                 470                 475                 480

Leu Asp Arg Asp Gly His Ile Lys Ile Ala Asp Phe Gly Met Cys Lys
                485                 490                 495

Glu Asn Ile Phe Gly Glu Ser Arg Ala Ser Thr Phe Cys Gly Thr Pro
            500                 505                 510

Asp Tyr Ile Ala Pro Glu Ile Leu Gln Gly Leu Lys Tyr Thr Phe Ser
        515                 520                 525

Val Asp Trp Trp Ser Phe Gly Val Leu Leu Tyr Glu Met Leu Ile Gly
    530                 535                 540

Gln Ser Pro Phe His Gly Asp Glu Asp Glu Leu Phe Glu Ser Ile
545                 550                 555                 560

Arg Val Asp Thr Pro His Tyr Pro Arg Trp Ile Thr Lys Glu Ser Lys
                565                 570                 575

Asp Ile Leu Glu Lys Leu Phe Glu Arg Glu Pro Thr Lys Arg Leu Gly
            580                 585                 590

Val Thr Gly Asn Ile Lys Ile His Pro Phe Phe Lys Thr Ile Asn Trp
        595                 600                 605

Thr Leu Leu Glu Lys Arg Arg Leu Glu Pro Pro Phe Arg Pro Lys Val
    610                 615                 620
```

Lys Ser Pro Arg Asp Tyr Ser Asn Phe Asp Gln Glu Phe Leu Asn Glu
625                 630                 635                 640

Lys Ala Arg Leu Ser Tyr Ser Asp Lys Asn Leu Ile Asp Ser Met Asp
            645                 650                 655

Gln Ser Ala Phe Ala Gly Phe Ser Phe Val Asn Pro Lys Phe Glu His
        660                 665                 670

Leu Leu Glu Asp
    675

<210> SEQ ID NO 8
<211> LENGTH: 2028
<212> TYPE: DNA
<213> ORGANISM: Artificial Sequence
<220> FEATURE:
<223> OTHER INFORMATION: Human Protein kinase C mutant, TMD

<400> SEQUENCE: 8

| | | | | | |
|---|---|---|---|---|---|
| atggcgccgt | tcctgcgcat | cgccttcaac | tcctatgagc | tgggctccct | gcaggccgag | 60 |
| gacgaggcga | accagccctt | ctgtgccgtg | aagatgaagg | aggcgctcag | cacagagcgt | 120 |
| gggaaaacac | tggtgcagaa | gaagccgacc | atgtatcctg | agtggaagtc | gacgttcgac | 180 |
| gcccacatct | atgagggcg | cgtcatccag | attgtgctaa | tgcgggcagc | agaggagcca | 240 |
| gtgtctgagg | tgaccgtggg | tgtgtcggtg | ctggccgagc | gctgcaagaa | gaacaatggc | 300 |
| aaggctgagt | tctggctgga | cctgcagcct | caggccaagg | tgttgatgtc | tgttcagtat | 360 |
| ttcctggagg | acgtggattg | caaacagtct | atgcgcagtg | aggacgaggc | caagttccca | 420 |
| acgatgaacc | gccgcggagc | catcaaacag | gccaaaatcc | actacatcaa | gaaccatgag | 480 |
| tttatcgcca | ccttctttgg | gcaacccacc | ttctgttctg | tgtgcaaaga | ctttgtctgg | 540 |
| ggcctcaaca | agcaaggcta | caatgcagg | caatgtaacg | ctgccatcca | caagaaatgc | 600 |
| atcgacaaga | tcatcggcag | atgcactggc | accgcggcca | cagccgggaa | cactatattc | 660 |
| cagaaagaac | gcttcaacat | cgacatgccg | caccgcttca | aggttcacaa | ctacatgagc | 720 |
| cccaccttct | gtgaccactg | cggcagcctg | ctctggggac | tggtgaagca | gggattaaag | 780 |
| tgtgaagact | gcggcatgaa | tgtgcaccat | aaatgccggg | agaaggtggc | caacctctgc | 840 |
| ggcatcaacc | agaagctttt | ggctgaggcc | ttgaaccaag | tcacccagag | agcctcccgg | 900 |
| agatcagact | cagcctcctc | agagcctgtt | gggatatttc | agggtttcga | agaagaccc | 960 |
| ggagttgctg | ggaggacat | gcaagacaac | agtgggacct | acggcaagat | ctgggagggc | 1020 |
| agcagcaagt | gcaacatcaa | caacttcatc | ttccacaagg | tcctgggcaa | aggcagcttc | 1080 |
| gggaaggtgc | tgcttggaga | gctgaagggc | agaggagagt | actttgccat | cagggcctc | 1140 |
| aagaaggatg | tggtcctgat | cgacgacgac | gtggagtgca | ccatggttga | aagcgggtg | 1200 |
| ctgacacttg | ccgcagagaa | tccctttctc | acccacctca | tctgcacctt | ccagaccaag | 1260 |
| gaccacctgt | tctttgtgat | ggagttcctc | aacgggggg | acctgatgta | ccacatccag | 1320 |
| gacaaaggcc | gcttttgaact | ctaccgtgcc | acgttttatg | ccgctgagat | aatgtgtgga | 1380 |
| ctgcagtttc | tacacagcaa | gggcatcatt | tacagggacc | tcaaactgga | caatgtgctg | 1440 |
| ttggaccggg | atggccacat | caagattgcc | gactttggga | tgtgcaaaga | gaacatattc | 1500 |
| ggggagagcc | gggccagcac | cttctgcggc | acccctgact | atatcgcccc | tgagatccta | 1560 |
| cagggcctga | gtacacatt | tctctgtgga | ctggtggtctt | tcgggtcct | tctgtacgag | 1620 |
| atgctcattg | gccagtcccc | cttccatggt | gatgatgagg | atgaactctt | cgagtccatc | 1680 |

```
cgtgtggaca cgccacatta tccccgctgg atcaccaagg agtccaagga catcctggag    1740
aagctctttg aaagggaacc aaccaagagg ctgggagtga cgggaaacat caaaatccac    1800
cccttcttca agaccataaa ctggactctg ctggaaaagc ggaggttgga gccacccttc    1860
aggcccaaag tgaagtcacc cagagactac agtaactttg accaggagtt cctgaacgag    1920
aaggcgcgcc tctcctacag cgacaagaac ctcatcgact ccatggacca gtctgcattc    1980
gctggcttct cctttgtgaa ccccaaattc gagcacctcc tggaagat               2028
```

<210> SEQ ID NO 9
<211> LENGTH: 239
<212> TYPE: PRT
<213> ORGANISM: Artificial Sequence
<220> FEATURE:
<223> OTHER INFORMATION: Labeling material, Enhanced Green Fluorescent
      Protein

<400> SEQUENCE: 9

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 10
<211> LENGTH: 716
<212> TYPE: DNA
<213> ORGANISM: Artificial Sequence
<220> FEATURE:
<223> OTHER INFORMATION: Labeling material for Enhanced Green
      Fluorescent Protein

<400> SEQUENCE: 10

```
tggtgagcaa gggcgaggag ctgttcaccg gggtggtgcc catcctggtc gagctggacg      60
gcgacgtaaa cggccacaag ttcagcgtgt ccggcgaggg cgagggcgat gccacctacg     120
gcaagctgac cctgaagttc atcctgcacc accggcaagct gcccgtgccc tggcccaccc   180
tcgtgaccac cctgacctac ggcgtgcagt gcttcagccg ctaccccgac acatgaagc     240 agcacgactt cttcaagtcc gccatgcccg aaggctacgt ccaggagcgc accatcttct   300
tcaaggacga cggcaactac aagacccgcg ccgaggtgaa gttcgagggc gacaccctgg   360
tgaaccgcat cgagctgaag ggcatcgact tcaaggagga cggcaacatc ctggggcaca   420
agctggagta caactacaac agccacaacg tctatatcat ggccgacaag cagaagaacg   480
gcatcaaggt gaacttcaag atccgccaca acatcgagga cggcagcgtg cagctcgccg   540
accactacca gcagaacacc cccatcggcg acggccccgt gctgctgccc gacaaccact   600
acctgagcac ccagtccgcc ctgagcaaag accccaacga gaagcgcgat cacatggtcc   660
tgctggagtt cgtgaccgcc gccgggatca ctctcggcat ggacgagctg tacaag       716
```

<210> SEQ ID NO 11
<211> LENGTH: 225
<212> TYPE: PRT
<213> ORGANISM: Artificial Sequence
<220> FEATURE:
<223> OTHER INFORMATION: Labeling material, Monomeric Red Fluorescent
      Protein

<400> SEQUENCE: 11

```
Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225
```

<210> SEQ ID NO 12
<211> LENGTH: 674
<212> TYPE: DNA
<213> ORGANISM: Artificial Sequence
<220> FEATURE:
<223> OTHER INFORMATION: Labeling material, Monomeric Red Fluorescent
      Protein

<400> SEQUENCE: 12

```
tggcctcctc cgaggacgtc atcaaggagt tcatgcgctt caaggtgcgc atggagggct      60
ccgtgaacgg ccacgagttc gagatcgagg gcgagggcga gggccgcccc tacgagggca     120
cccagaccgc caagctgaag gtgaccaagg gcggccccct gcccttcgcc tgggacatcc     180
tgtcccctca gttccagtac ggctccaagg cctacgtgaa gcaccccgcc gacatccccg     240
actacttgaa gctgtccttc cccgagggct tcaagtggga gcgcgtgatg aacttcgagg     300
acggcggcgt ggtgaccgtg acccaggact cctccctgca ggacggcgag ttcatctaca     360
aggtgaagct gcgcggcacc aacttcccct ccgacggccc cgtaatgcag aagaagacca     420
tgggctggga ggcctccacc gagcggatgt accccgagga cggcgccctg aagggcgaga     480
tcaagatgag gctgaagctg aaggacggcg gccactacga cgccgaggtc aagaccacct     540
acatggccaa gaagcccgtg cagctgcccg gcgcctacaa gaccgacatc aagctggaca     600
tcacctccca caacgaggac tacaccatcg tggaacagta cgagcgcgcc gagggccgcc     660
actccaccgg cgcc                                                       674
```

<210> SEQ ID NO 13
<211> LENGTH: 229
<212> TYPE: PRT
<213> ORGANISM: Artificial Sequence
<220> FEATURE:
<223> OTHER INFORMATION: Labeling material, Azami Green

<400> SEQUENCE: 13

```
Met Asp Pro Met Val Ser Val Ile Lys Pro Glu Met Lys Ile Lys Leu
1               5                   10                  15

Cys Met Arg Gly Thr Val Asn Gly His Asn Phe Val Ile Glu Gly Glu
            20                  25                  30

Gly Lys Gly Asn Pro Tyr Glu Gly Thr Gln Ile Leu Asp Leu Asn Val
        35                  40                  45

Thr Glu Gly Ala Pro Leu Pro Phe Ala Tyr Asp Ile Leu Thr Thr Val
    50                  55                  60

Phe Gln Tyr Gly Asn Arg Ala Phe Thr Lys Tyr Pro Ala Asp Ile Gln
65                  70                  75                  80

Asp Tyr Phe Lys Gln Thr Phe Pro Glu Gly Tyr His Trp Glu Arg Ser
                85                  90                  95

Met Thr Tyr Glu Asp Gln Gly Ile Cys Thr Ala Thr Ser Asn Ile Ser
            100                 105                 110

Met Arg Gly Asp Cys Phe Phe Tyr Asp Ile Arg Phe Asp Gly Thr Asn
        115                 120                 125

Phe Pro Pro Asn Gly Pro Val Met Gln Lys Lys Thr Leu Lys Trp Glu
    130                 135                 140

Pro Ser Thr Glu Lys Met Tyr Val Glu Asp Gly Val Leu Lys Gly Asp
145                 150                 155                 160

Val Asn Met Arg Leu Leu Leu Glu Gly Gly Gly His Tyr Arg Cys Asp
                165                 170                 175
```

```
Phe Lys Thr Thr Tyr Lys Ala Lys Lys Glu Val Arg Leu Pro Asp Ala
            180                 185                 190

His Lys Ile Asp His Arg Ile Glu Ile Leu Lys His Asp Lys Asp Tyr
        195                 200                 205

Asn Lys Val Lys Leu Tyr Glu Asn Ala Val Ala Arg Tyr Ser Met Leu
        210                 215                 220

Pro Ser Gln Ala Lys
225

<210> SEQ ID NO 14
<211> LENGTH: 687
<212> TYPE: DNA
<213> ORGANISM: Artificial Sequence
<220> FEATURE:
<223> OTHER INFORMATION: Labeling material, Azami Green

<400> SEQUENCE: 14
atggacccca tggtgagtgt gattaaacca gagatgaaga tcaagctgtg tatgagaggc      60
actgtaaacg ggcataattt cgtgattgaa ggagaaggaa aaggaaatcc ttacgaggga     120
acgcagattt tagacctgaa cgtcactgaa ggcgcacctc tgcctttcgc ttacgatatc     180
ttgacaacag tgttccagta cggcaacagg gcattcacca gtacccagc agatattcag      240 gactatttca gcagactttt tcctgagggg tatcactggg aaagaagcat gacttatgaa     300
gaccagggca tttgcaccgc acaagcaac ataagcatga gggcgactg ttttttctat       360 gacattcgtt tgatggcac caactttcct cccaatggtc cggttatgca agaagagact      420
cttaaatggg agccatccac tgagaaaatg tacgtagagg atggagtgct gaagggtgat     480
gttaacatgc gcctgttgct tgaaggaggt ggccattatc gatgtgattt caaaactact     540
tacaaagcaa agaaggaggt ccgtttgcca gacgcgcaca aaattgacca ccgcattgag     600
attttgaagc atgacaaaga ttacaacaag gtcaagctct atgagaatgc cgttgctcgc     660
tattctatgc tgccgagtca ggccaag                                         687

<210> SEQ ID NO 15
<211> LENGTH: 228
<212> TYPE: PRT
<213> ORGANISM: Artificial Sequence
<220> FEATURE:
<223> OTHER INFORMATION: Labeling material, Heteractis crispa red
      fluorescent protein

<400> SEQUENCE: 15

Met Val Ser Gly Leu Leu Lys Glu Ser Met Arg Ile Lys Met Tyr Met
1               5                   10                  15

Glu Gly Thr Val Asn Gly His Tyr Phe Lys Cys Glu Gly Glu Gly Asp
            20                  25                  30

Gly Asn Pro Phe Ala Gly Thr Gln Ser Met Arg Ile His Val Thr Glu
        35                  40                  45

Gly Ala Pro Leu Pro Phe Ala Phe Asp Ile Leu Ala Pro Cys Cys Glu
    50                  55                  60

Tyr Gly Ser Arg Thr Phe Val His His Thr Ala Glu Ile Pro Asp Phe
65                  70                  75                  80

Phe Lys Gln Ser Phe Pro Glu Gly Phe Thr Trp Glu Arg Thr Thr Thr
                85                  90                  95

Tyr Glu Asp Gly Gly Ile Leu Thr Ala His Gln Asp Thr Ser Leu Glu
            100                 105                 110

Gly Asn Cys Leu Ile Tyr Lys Val Lys Val His Gly Thr Asn Phe Pro
```

```
                115                 120                 125
Ala Asp Gly Pro Val Met Lys Asn Lys Ser Gly Gly Trp Glu Pro Ser
        130                 135                 140

Thr Glu Val Val Tyr Pro Glu Asn Gly Val Leu Cys Gly Arg Asn Val
145                 150                 155                 160

Met Ala Leu Lys Val Gly Asp Arg His Leu Ile Cys His His Tyr Thr
                165                 170                 175

Ser Tyr Arg Ser Lys Lys Ala Val Arg Ala Leu Thr Met Pro Gly Phe
            180                 185                 190

His Phe Thr Asp Ile Arg Leu Gln Met Leu Arg Lys Lys Asp Glu
        195                 200                 205

Tyr Phe Glu Leu Tyr Glu Ala Ser Val Ala Arg Tyr Ser Asp Leu Pro
    210                 215                 220

Glu Lys Ala Asn
225

<210> SEQ ID NO 16
<211> LENGTH: 684
<212> TYPE: DNA
<213> ORGANISM: Artificial Sequence
<220> FEATURE:
<223> OTHER INFORMATION: Labeling material, Heteractis crispa red
      fluorescent protein

<400> SEQUENCE: 16
atggtgagcg gcctgctgaa ggagagtatg cgcatcaaga tgtacatgga gggcaccgtg      60
aacggccact acttcaagtg cgagggcgag ggcgacggca ccccttcgc cggcacccag      120
agcatgagaa tccacgtgac cgagggcgcc cccctgccct tcgccttcga catcctggcc     180
ccctgctgcg agtacggcag caggaccttc gtgcaccaca ccgccgagat ccccgacttc     240
ttcaagcaga gcttccccga gggcttcacc tgggagagaa ccaccaccta cgaggacggc     300
ggcatcctga ccgcccacca ggacaccagc ctggagggca ctgcctgat ctacaaggtg      360
aaggtgcacg gcaccaactt ccccgccgac ggccccgtga tgaagaacaa gagcggcggc     420
tgggagccca gcaccgaggt ggtgtacccc gagaacggcg tgctgtgcgg ccggaacgtg     480
atggccctga aggtgggcga ccggcacctg atctgccacc actacaccag ctaccggagc     540
aagaaggccg tgcgcgccct gaccatgccc ggcttccact tcaccgacat ccggctccag     600
atgctgcgga agaagaagga cgagtacttc gagctgtacg aggccagcgt ggcccggtac     660
agcgacctgc ccgagaaggc caac                                             684

<210> SEQ ID NO 17
<211> LENGTH: 23
<212> TYPE: PRT
<213> ORGANISM: Artificial Sequence
<220> FEATURE:
<223> OTHER INFORMATION: Nuclear Localization Signal (NLS) for construct

<400> SEQUENCE: 17

Gly Ser Gly Asp Glu Val Glu Gly Val Glu Glu Val Ala Lys Lys Lys
1               5                   10                  15

Ser Lys Lys Glu Lys Asp Lys
            20

<210> SEQ ID NO 18
<211> LENGTH: 69
<212> TYPE: DNA
<213> ORGANISM: Artificial Sequence
```

```
<220> FEATURE:
<223> OTHER INFORMATION: Nuclear Localization Signal (NLS) for construct

<400> SEQUENCE: 18
ggctctggtg atgaagtcga aggagtggaa gaagtagcta agaagaagag taaaaaggaa      60
aaggataaa                                                             69

<210> SEQ ID NO 19
<211> LENGTH: 18
<212> TYPE: PRT
<213> ORGANISM: Artificial Sequence
<220> FEATURE:
<223> OTHER INFORMATION: Nuclear export Signal(NES) for construct

<400> SEQUENCE: 19

Asp Gln Arg Val Ile Ile Lys Leu Asn Ala His Val Gly Asn Ile Ser
1               5                   10                  15

Leu Val

<210> SEQ ID NO 20
<211> LENGTH: 54
<212> TYPE: DNA
<213> ORGANISM: Artificial Sequence
<220> FEATURE:
<223> OTHER INFORMATION: Nuclear export Signal(NES) for construct

<400> SEQUENCE: 20
gaccagcgcg tcatcatcaa gctgaacgcc catgtgggaa acatttccct ggtg           54

<210> SEQ ID NO 21
<211> LENGTH: 4727
<212> TYPE: DNA
<213> ORGANISM: Artificial Sequence
<220> FEATURE:
<223> OTHER INFORMATION: pEGFP-C3 vector-GenBank Accession No. U57607

<400> SEQUENCE: 21
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacg caaatgggcg taggcgtgt     540 acggtgggag gtctatataa gcagagctgg tttagtgaac cgtcagatcc gctagcgcta    600
ccggtcgcca ccatggtgag caagggcgag gagctgttca ccggggtggt gcccatcctg    660
gtcgagctgg acggcgacgt aaacggccac aagttcagcg tgtccggcga gggcgagggc    720
gatgccacct acggcaagct gaccctgaag ttcatctgca ccaccggcaa gctgcccgtg    780
ccctggccca ccctcgtgac caccctgacc tacggcgtgc agtgcttcag ccgctacccc    840
gaccacatga agcagcacga cttcttcaag tccgccatgc ccgaaggcta cgtccaggag    900
cgcaccatct tcttcaagga cgacggcaac tacaagaccc gcgccgaggt gaagttcgag    960
ggcgacaccc tggtgaaccg catcgagctg aagggcatcg acttcaagga ggacggcaac   1020
```

```
atcctggggc acaagctgga gtacaactac aacagccaca acgtctatat catggccgac    1080
aagcagaaga acggcatcaa ggtgaacttc aagatccgcc acaacatcga ggacggcagc    1140
gtgcagctcg ccgaccacta ccagcagaac acccccatcg gcgacggccc cgtgctgctg    1200
cccgacaacc actacctgag cacccagtcc gccctgagca agaccccaa cgagaagcgc     1260 gatcacatgg tcctgctgga gttcgtgacc gccgccggga tcactctcgg catggacgag    1320
ctgtacaagt actcagatct cgagctcaag cttcgaattc tgcagtcgac ggtaccgcgg    1380
gcccgggatc caccggatct agataactga tcataatcag ccataccaca tttgtagagg    1440
ttttacttgc tttaaaaaac ctcccacacc tccccctgaa cctgaaacat aaaatgaatg    1500
caattgttgt tgttaacttg tttattgcag cttataatgg ttacaaataa agcaatagca    1560
tcacaaattt cacaaataaa gcatttttt cactgcattc tagttgtggt ttgtccaaac     1620
tcatcaatgt atcttaacgc gtaaattgta agcgttaata ttttgttaaa attcgcgtta    1680 aattttgtt aaatcagctc attttttaac caataggccg aaatcggcaa aatcccttat     1740
aaatcaaaag aatagaccga datagggttg agtgttgttc cagtttggaa caagagtcca    1800
ctattaaaga acgtggactc caacgtcaaa gggcgaaaaa ccgtctatca gggcgatggc    1860
ccactacgtg aaccatcacc ctaatcaagt tttttggggt cgaggtgccg taaagcacta    1920
aatcggaacc ctaaagggag cccccgattt agagcttgac ggggaaagcc ggcgaacgtg    1980
gcgagaaagg aagggaagaa agcgaaagga gcgggcgcta gggcgctggc aagtgtagcg    2040
gtcacgctgc gcgtaaccac cacacccgcc gcgcttaatg cgccgctaca gggcgcgtca    2100
ggtggcactt ttcggggaaa tgtgcgcgga acccctattt gtttattttt ctaaatacat    2160
tcaaatatgt atccgctcat gagacaataa ccctgataaa tgcttcaata atattgaaaa    2220
aggaagagtc ctgaggcgga aagaaccagc tgtggaatgt gtgtcagtta gggtgtggaa    2280
agtccccagg ctccccagca ggcagaagta tgcaaagcat gcatctcaat tagtcagcaa    2340
ccaggtgtgg aaagtcccca ggctccccag caggcagaag tatgcaaagc atgcatctca    2400
attagtcagc aaccatagtc ccgcccctaa ctccgcccat cccgcccta actccgccca    2460 gttccgccca ttctccgccc catggctgac taatttttt tatttatgca gaggccgagg     2520
ccgcctcggc ctctgagcta ttccagaagt agtgaggagg cttttttgga ggcctaggct    2580
tttgcaaaga tcgatcaaga dacaggatga ggatcgtttc gcatgattga acaagatgga    2640
ttgcacgcag gttctccggc cgcttgggtg gagaggctat tcggctatga ctgggcacaa    2700
cagacaatcg gctgctctga tgccgccgtg ttccggctgt cagcgcaggg gcgcccggtt    2760 cttttgtca agaccgacct gtccggtgcc ctgaatgaac tgcaagacga ggcagcgcgg     2820
ctatcgtggc tggccacgac gggcgttcct tgcgcagctg tgctcgacgt tgtcactgaa    2880
gcgggaaggg actggctgct attgggcgaa gtgccggggc aggatctcct gtcatctcac    2940
cttgctcctg ccgagaaagt atccatcatg gctgatgcaa tgcggcggct gcatacgctt    3000
gatccggcta cctgcccatt cgaccaccaa gcgaaacatc gcatcgagcg agcacgtact    3060
cggatggaag ccggtcttgt cgatcaggat gatctggacg aagagcatca ggggctcgcg    3120
ccagccgaac tgttcgccag gctcaaggcg agcatgcccg acggcgagga tctcgtcgtg    3180
acccatggcg atgcctgctt gccgaatatc atggtggaaa atggccgctt tctggattca    3240
atcgactgtg gccggctggg tgtggcggac cgctatcagg acatagcgtt ggctacccgt    3300
gatattgctg aagagcttgg cggcgaatgg gctgaccgct tcctcgtgct ttacggtatc    3360
```

-continued

```
gccgctcccg attcgcagcg catcgccttc tatcgccttc ttgacgagtt cttctgagcg   3420
ggactctggg gttcgaaatg accgaccaag cgacgcccaa cctgccatca cgagatttcg   3480
attccaccgc cgccttctat gaaaggttgg gcttcggaat cgttttccgg gacgccggct   3540
ggatgatcct ccagcgcggg gatctcatgc tggagttctt cgcccaccct agggggaggc   3600
taactgaaac acggaaggag acaataccgg aaggaacccg cgctatgacg gcaataaaaa   3660
gacagaataa aacgcacggt gttgggtcgt ttgttcataa acgcggggtt cggtcccagg   3720
gctggcactc tgtcgatacc ccaccgagac cccattgggg ccaatacgcc cgcgtttctt   3780
ccttttcccc accccacccc ccaagttcgg gtgaaggccc agggctcgca gccaacgtcg   3840
gggcggcagg ccctgccata gcctcaggtt actcatatat actttagatt gatttaaaac   3900
ttcattttta atttaaaagg atctaggtga agatcctttt tgataatctc atgaccaaaa   3960
tcccttaacg tgagttttcg ttccactgag cgtcagaccc cgtagaaaag atcaaaggat   4020
cttcttgaga tccttttttt ctgcgcgtaa tctgctgctt gcaaacaaaa aaaccaccgc   4080
taccagcggt ggtttgtttg ccggatcaag agctaccaac tctttttccg aaggtaactg   4140
gcttcagcag agcgcagata ccaaatactg tccttctagt gtagccgtag ttaggccacc   4200
acttcaagaa ctctgtagca ccgcctacat acctcgctct gctaatcctg ttaccagtgg   4260
ctgctgccag tggcgataag tcgtgtctta ccgggttgga ctcaagacga tagttaccgg   4320
ataaggcgca gcggtcgggc tgaacggggg gttcgtgcac acagcccagc ttggagcgaa   4380
cgacctacac cgaactgaga tacctacagc gtgagctatg agaaagcgcc acgcttcccg   4440
aagggagaaa ggcggacagg tatccggtaa gcggcagggt cggaacagga gagcgcacga   4500
gggagcttcc agggggaaac gcctggtatc tttatagtcc tgtcgggttt cgccacctct   4560
gacttgagcg tcgatttttg tgatgctcgt caggggggcg gagcctatgg aaaaacgcca   4620
gcaacgcggc ctttttacgg ttcctggcct tttgctggcc ttttgctcac atgttctttc   4680
ctgcgttatc ccctgattct gtggataacc gtattaccgc catgcat                 4727
```

<210> SEQ ID NO 22
<211> LENGTH: 4685
<212> TYPE: DNA
<213> ORGANISM: Artificial Sequence
<220> FEATURE:
<223> OTHER INFORMATION: pmRFP-C3 vector-GenBank Accession No. DQ903889

<400> SEQUENCE: 22

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggtcgcca ccatggcctc ctccgaggac gtcatcaagg agttcatgcg cttcaaggtg    660
cgcatggagg gctccgtgaa cggccacgag ttcgagatcg agggcgaggg cgagggccgc    720
```

```
ccctacgagg gcacccagac cgccaagctg aaggtgacca agggcggccc cctgcccttc    780
gcctgggaca tcctgtcccc tcagttccag tacggctcca aggcctacgt gaagcacccc    840
gccgacatcc ccgactactt gaagctgtcc ttccccgagg gcttcaagtg ggagcgcgtg    900
atgaacttcg aggacggcgg cgtggtgacc gtgacccagg actcctccct gcaggacggc    960
gagttcatct acaaggtgaa gctgcgcggc accaacttcc cctccgacgg ccccgtaatg   1020
cagaagaaga ccatgggctg ggaggcctcc accgagcgga tgtacccga ggacggcgcc    1080 ctgaagggcg agatcaagat gaggctgaag ctgaaggacg gcggccacta cgacgccgag    1140
gtcaagacca cctacatggc caagaagccc gtgcagctgc ccggcgccta caagaccgac    1200
atcaagctgg acatcaccct ccacaacgag gactacacca tcgtggaaca gtacgagcgc    1260
gccgagggcc gccactccac cggcgccctg tcagatctcg agctcaagct tcgaattctg    1320
cagtcgacgg taccgcgggc ccgggatcca ccggatctag ataactgatc ataatcagcc    1380
ataccacatt tgtagaggtt ttacttgctt taaaaaacct cccacacctc cccctgaacc    1440
tgaaacataa aatgaatgca attgttgttg ttaacttgtt tattgcagct tataatggtt    1500
acaaataaag caatagcatc acaaatttca caaataaagc atttttttca ctgcattcta    1560
gttgtggttt gtccaaactc atcaatgtat cttaacgcgt aaattgtaag cgttaatatt    1620
ttgttaaaat tcgcgttaaa tttttgttaa atcagctcat tttttaacca ataggccgaa    1680
atcggcaaaa tcccttataa atcaaaagaa tagaccgaga tagggttgag tgttgttcca    1740
gtttggaaca agagtccact attaaagaac gtggactcca acgtcaaagg gcgaaaaacc    1800
gtctatcagg gcgatggccc actacgtgaa ccatcaccct aatcaagttt tttggggtcg    1860
aggtgccgta aagcactaaa tcggaaccct aaagggagcc cccgatttag agcttgacgg    1920
ggaaagccgg cgaacgtggc gagaaaggaa gggaagaaag cgaaaggagc gggcgctagg    1980
gcgctggcaa gtgtagcggt cacgctgcgc gtaaccacca cacccgccgc gcttaatgcg    2040
ccgctacagg gcgcgtcagg tggcactttt cggggaaatg tgcgcggaac ccctatttgt    2100
ttatttttct aaatacattc aaatatgtat ccgctcatga gacaataacc ctgataaatg    2160
cttcaataat attgaaaaag gaagagtcct gaggcggaaa gaaccagctg tggaatgtgt    2220
gtcagttagg gtgtggaaag tccccaggct ccccagcagg cagaagtatg caaagcatgc    2280
atctcaatta gtcagcaacc aggtgtggaa agtcccagg ctccccagca ggcagaagta    2340
tgcaaagcat gcatctcaat tagtcagcaa ccatagtccc gcccctaact ccgcccatcc    2400
cgcccctaac tccgcccagt tccgcccatt ctccgcccca tggctgacta atttttttta    2460
tttatgcaga ggccgaggcc gcctcggcct ctgagctatt ccagaagtag tgaggaggct    2520 ttttttggagg cctaggcttt tgcaaagatc gatcaagaga caggatgagg atcgtttcgc    2580
atgattgaac aagatggatt gcacgcaggt tctccggccg cttgggtgga gaggctattc    2640
ggctatgact gggcacaaca gacaatcggc tgctctgatg ccgccgtgtt ccggctgtca    2700 gcgcagggc gcccggttct ttttgtcaag accgacctgt ccggtgccct gaatgaactg    2760
caagacgagg cagcgcggct atcgtggctg gccacgacgg gcgttccttg cgcagctgtg    2820
ctcgacgttg tcactgaagc gggaagggac tggctgctat tgggcgaagt gccggggcag    2880
gatctcctgt catctcacct tgctcctgcc gagaaagtat ccatcatggc tgatgcaatg    2940
cggcggctgc atacgcttga tccggctacc tgcccattcg accaccaagc gaaacatcgc    3000
atcgagcgag cacgtactcg gatggaagcc ggtcttgtcg atcaggatga tctggacgaa    3060
```

```
gagcatcagg ggctcgcgcc agccgaactg ttcgccaggc tcaaggcgag catgcccgac    3120
ggcgaggatc tcgtcgtgac ccatggcgat gcctgcttgc cgaatatcat ggtggaaaat    3180
ggccgctttt ctggattcat cgactgtggc cggctgggtg tggcggaccg ctatcaggac    3240
atagcgttgg ctacccgtga tattgctgaa gagcttggcg gcgaatgggc tgaccgcttc    3300
ctcgtgcttt acggtatcgc cgctcccgat tcgcagcgca tcgccttcta tcgccttctt    3360
gacgagttct tctgagcggg actctggggt tcgaaatgac cgaccaagcg acgcccaacc    3420
tgccatcacg agatttcgat tccaccgccg ccttctatga aaggttgggc ttcggaatcg    3480
ttttccggga cgccggctgg atgatcctcc agcgcgggga tctcatgctg gagttcttcg    3540
cccaccctag ggggaggcta actgaaacac ggaaggagac aataccggaa ggaacccgcg    3600
ctatgacggc aataaaaaga cagaataaaa cgcacggtgt tgggtcgttt gttcataaac    3660
gcggggttcg gtcccagggc tggcactctg tcgataccc accgagaccc cattggggcc    3720
aatacgcccg cgtttcttcc ttttccccac cccacccccc aagttcgggt gaaggcccag    3780
ggctcgcagc caacgtcggg gcggcaggcc ctgccatagc ctcaggttac tcatatatac    3840
tttagattga tttaaaactt cattttttaat ttaaaaggat ctaggtgaag atccttttttg   3900 ataatctcat gaccaaaatc ccttaacgtg agttttcgtt ccactgagcg tcagaccccg    3960
tagaaaagat caaaggatct tcttgagatc ctttttttct gcgcgtaatc tgctgcttgc    4020
aaacaaaaaa accaccgcta ccagcggtgg tttgtttgcc ggatcaagag ctaccaactc    4080 ttttccgaa ggtaactggc ttcagcagag cgcagatacc aaatactgtc cttctagtgt    4140
agccgtagtt aggccaccac ttcaagaact ctgtagcacc gcctacatac ctcgctctgc    4200
taatcctgtt accagtggct gctgccagtg gcgataagtc gtgtcttacc gggttggact    4260
caagacgata gttaccggat aaggcgcagc ggtcgggctg aacggggggt cgtgcacac    4320 agcccagctt ggagcgaacg acctacaccg aactgagata cctacagcgt gagctatgag    4380
aaagcgccac gcttcccgaa gggagaaagg cggacaggta tccggtaagc ggcagggtcg    4440
gaacaggaga gcgcacgagg gagcttccag ggggaaacgc ctggtatctt tatagtcctg    4500
tcgggtttcg ccacctctga cttgagcgtc gatttttgtg atgctcgtca ggggggcgga    4560
gcctatggaa aaacgccagc aacgcggcct ttttacggtt cctggccttt tgctggcctt    4620
ttgctcacat gttctttcct gcgttatccc ctgattctgt ggataaccgt attaccgcca    4680
tgcat                                                              4685
```

<210> SEQ ID NO 23
<211> LENGTH: 32
<212> TYPE: DNA
<213> ORGANISM: Artificial Sequence
<220> FEATURE:
<223> OTHER INFORMATION: Forward primer for PRKCD

<400> SEQUENCE: 23
gaagctagcc gccaccatgg cgccgttcct gc                                   32

<210> SEQ ID NO 24
<211> LENGTH: 37
<212> TYPE: DNA
<213> ORGANISM: Artificial Sequence
<220> FEATURE:
<223> OTHER INFORMATION: Reverse primer for PRKCD

<400> SEQUENCE: 24
gaaaccggtg gatcttccag gaggtgctcg aatttgg                              37

<210> SEQ ID NO 25
<211> LENGTH: 43
<212> TYPE: DNA
<213> ORGANISM: Artificial Sequence
<220> FEATURE:
<223> OTHER INFORMATION: Forward primer for TMA

<400> SEQUENCE: 25
gaagctagcc gccaccatga acaggccaa aatccactac atc                43

<210> SEQ ID NO 26
<211> LENGTH: 32
<212> TYPE: DNA
<213> ORGANISM: Artificial Sequence
<220> FEATURE:
<223> OTHER INFORMATION: Reverse primer for TMA

<400> SEQUENCE: 26
gaaaccggtg gagtgtcccg gctgttggcc gc                           32

<210> SEQ ID NO 27
<211> LENGTH: 41
<212> TYPE: DNA
<213> ORGANISM: Artificial Sequence
<220> FEATURE:
<223> OTHER INFORMATION: Forward primer for TMB

<400> SEQUENCE: 27
gcagctagcc gccaccatgc agaaagaacg cttcaacatc g                 41

<210> SEQ ID NO 28
<211> LENGTH: 32
<212> TYPE: DNA
<213> ORGANISM: Artificial Sequence
<220> FEATURE:
<223> OTHER INFORMATION: Reverse primer for TMB

<400> SEQUENCE: 28
gcaaccggtg gggcctcagc caaaagcttc tg                           32

<210> SEQ ID NO 29
<211> LENGTH: 32
<212> TYPE: DNA
<213> ORGANISM: Artificial Sequence
<220> FEATURE:
<223> OTHER INFORMATION: Forward primer for PKCD

<400> SEQUENCE: 29
gaagctagcc gccaccatgg cgccgttcct gc                           32

<210> SEQ ID NO 30
<211> LENGTH: 21
<212> TYPE: DNA
<213> ORGANISM: Artificial Sequence
<220> FEATURE:
<223> OTHER INFORMATION: Reverse primer for Y313F

<400> SEQUENCE: 30
gaaaccctga aatatcccaa c                                       21

<210> SEQ ID NO 31
<211> LENGTH: 21
<212> TYPE: DNA
<213> ORGANISM: Artificial Sequence
<220> FEATURE:

<223> OTHER INFORMATION: Forward primer for Y313F

<400> SEQUENCE: 31
gttgggatat tcagggtttt c                                          21

<210> SEQ ID NO 32
<211> LENGTH: 37
<212> TYPE: DNA
<213> ORGANISM: Artificial Sequence
<220> FEATURE:
<223> OTHER INFORMATION: Reverse primer for PKCD

<400> SEQUENCE: 32
gaaaccggtg gatcttccag gaggtgctcg aatttgg                         37

<210> SEQ ID NO 33
<211> LENGTH: 21
<212> TYPE: DNA
<213> ORGANISM: Artificial Sequence
<220> FEATURE:
<223> OTHER INFORMATION: Forward primer for K378R

<400> SEQUENCE: 33
tttgccatca gggccctcaa g                                          21

<210> SEQ ID NO 34
<211> LENGTH: 21
<212> TYPE: DNA
<213> ORGANISM: Artificial Sequence
<220> FEATURE:
<223> OTHER INFORMATION: Reverse primer for K378R

<400> SEQUENCE: 34
cttgagggcc ctgatggcaa a                                          21

<210> SEQ ID NO 35
<211> LENGTH: 44
<212> TYPE: DNA
<213> ORGANISM: Artificial Sequence
<220> FEATURE:
<223> OTHER INFORMATION: Forward primer 1 for NLS

<400> SEQUENCE: 35
agtaaaaagg aaaaggataa atagataact gatcataatc agcc                 44

<210> SEQ ID NO 36
<211> LENGTH: 23
<212> TYPE: DNA
<213> ORGANISM: Artificial Sequence
<220> FEATURE:
<223> OTHER INFORMATION: Reverse primer for NLS

<400> SEQUENCE: 36
gctgcaataa acaagttaac aac                                        23

<210> SEQ ID NO 37
<211> LENGTH: 44
<212> TYPE: DNA
<213> ORGANISM: Artificial Sequence
<220> FEATURE:
<223> OTHER INFORMATION: Forward primer 2 for NLS

<400> SEQUENCE: 37
tggaagaagt agctaagaag aagagtaaaa aggaaaagga taaa                 44

```
<210> SEQ ID NO 38
<211> LENGTH: 44
<212> TYPE: DNA
<213> ORGANISM: Artificial Sequence
<220> FEATURE:
<223> OTHER INFORMATION: Forward primer 3 for NLS

<400> SEQUENCE: 38
tccggtgatg aagtcgaagg agtggaagaa gtagctaaga agaa            44

<210> SEQ ID NO 39
<211> LENGTH: 33
<212> TYPE: DNA
<213> ORGANISM: Artificial Sequence
<220> FEATURE:
<223> OTHER INFORMATION: Forward primer 4 for NLS

<400> SEQUENCE: 39
gctggatcca ggctctggtg atgaagtcga agg            33

<210> SEQ ID NO 40
<211> LENGTH: 44
<212> TYPE: DNA
<213> ORGANISM: Artificial Sequence
<220> FEATURE:
<223> OTHER INFORMATION: Forward primer 1 for NES

<400> SEQUENCE: 40
gtgggaaaca tttccctggt gtagataact gatcataatc agcc            44

<210> SEQ ID NO 41
<211> LENGTH: 23
<212> TYPE: DNA
<213> ORGANISM: Artificial Sequence
<220> FEATURE:
<223> OTHER INFORMATION: Reverse primer for NES

<400> SEQUENCE: 41
gctgcaataa acaagttaac aac            23

<210> SEQ ID NO 42
<211> LENGTH: 44
<212> TYPE: DNA
<213> ORGANISM: Artificial Sequence
<220> FEATURE:
<223> OTHER INFORMATION: Forward primer 2 for NES

<400> SEQUENCE: 42
gtcatcatca agctgaacgc ccatgtggga aacatttccc tggt            44

<210> SEQ ID NO 43
<211> LENGTH: 40
<212> TYPE: DNA
<213> ORGANISM: Artificial Sequence
<220> FEATURE:
<223> OTHER INFORMATION: Forward primer 3 for NES

<400> SEQUENCE: 43
gtcggatcca gaccagcgcg tcatcatcaa gctgaacgcc            40

<210> SEQ ID NO 44
<211> LENGTH: 39
<212> TYPE: DNA
<213> ORGANISM: Artificial Sequence
<220> FEATURE:
<223> OTHER INFORMATION: Forward primer for Azami Green
```

<400> SEQUENCE: 44
ggcaccggtc gccaccatgg accccatggt gagtgtgat          39

<210> SEQ ID NO 45
<211> LENGTH: 35
<212> TYPE: DNA
<213> ORGANISM: Artificial Sequence
<220> FEATURE:
<223> OTHER INFORMATION: Reverse primer for Azami Green

<400> SEQUENCE: 45
ggcagatctg acagcttggc ctgactcggc agcat          35

<210> SEQ ID NO 46
<211> LENGTH: 24
<212> TYPE: DNA
<213> ORGANISM: Artificial Sequence
<220> FEATURE:
<223> OTHER INFORMATION: Forward primer for Heteractis crispa red
      fluorescent protein

<400> SEQUENCE: 46
gccaccggtc gccaccatgg tgag          24

<210> SEQ ID NO 47
<211> LENGTH: 38
<212> TYPE: DNA
<213> ORGANISM: Artificial Sequence
<220> FEATURE:
<223> OTHER INFORMATION: Reverse primer for Heteractis crispa red
      fluorescent protein

<400> SEQUENCE: 47
gccgcggccg cttatcagtt ggccttctcg ggcaggtc          38

<210> SEQ ID NO 48
<211> LENGTH: 35
<212> TYPE: DNA
<213> ORGANISM: Artificial Sequence
<220> FEATURE:
<223> OTHER INFORMATION: Forward primer for p53

<400> SEQUENCE: 48
gaagaattct gatgcctgtc accgagaccc ctggg          35

<210> SEQ ID NO 49
<211> LENGTH: 34
<212> TYPE: DNA
<213> ORGANISM: Artificial Sequence
<220> FEATURE:
<223> OTHER INFORMATION: Reverse primer for p53

<400> SEQUENCE: 49
gaaggatccc gtcagtctga gtcaggcccc actt          34

<210> SEQ ID NO 50
<211> LENGTH: 35
<212> TYPE: DNA
<213> ORGANISM: Artificial Sequence
<220> FEATURE:
<223> OTHER INFORMATION: Forward primer for SV40T

<400> SEQUENCE: 50
gaagaattct gatgggaact gatgaatggg agcag          35

<210> SEQ ID NO 51
<211> LENGTH: 32
<212> TYPE: DNA
<213> ORGANISM: Artificial Sequence
<220> FEATURE:
<223> OTHER INFORMATION: Reverse primer for SV40T

<400> SEQUENCE: 51
gaaggatccc gttatgtttc aggttcaggg gg                32

<210> SEQ ID NO 52
<211> LENGTH: 30
<212> TYPE: DNA
<213> ORGANISM: Artificial Sequence
<220> FEATURE:
<223> OTHER INFORMATION: Forward primer for p38

<400> SEQUENCE: 52
gtcctcgaga tgccgatgta ccaggtaaag                30

<210> SEQ ID NO 53
<211> LENGTH: 30
<212> TYPE: DNA
<213> ORGANISM: Artificial Sequence
<220> FEATURE:
<223> OTHER INFORMATION: Reverse primer for p38

<400> SEQUENCE: 53
gtcggatcct taaaaggag ccaggttttc                30

<210> SEQ ID NO 54
<211> LENGTH: 32
<212> TYPE: DNA
<213> ORGANISM: Artificial Sequence
<220> FEATURE:
<223> OTHER INFORMATION: Forward primer for Gag

<400> SEQUENCE: 54
gtcgaattct gatgggtgcg agagcgtcag ta                32

<210> SEQ ID NO 55
<211> LENGTH: 30
<212> TYPE: DNA
<213> ORGANISM: Artificial Sequence
<220> FEATURE:
<223> OTHER INFORMATION: Reverse primer for Gag

<400> SEQUENCE: 55
gtcggatcct tattgtgacg aggggtcgtt                30

<210> SEQ ID NO 56
<211> LENGTH: 31
<212> TYPE: DNA
<213> ORGANISM: Artificial Sequence
<220> FEATURE:
<223> OTHER INFORMATION: Forward primer for LR

<400> SEQUENCE: 56
gtcgaattct gatgtccgga gcccttgatg t                31

<210> SEQ ID NO 57
<211> LENGTH: 32
<212> TYPE: DNA
<213> ORGANISM: Artificial Sequence
<220> FEATURE:
<223> OTHER INFORMATION: Reverse primer for LR

```
<400> SEQUENCE: 57
gtcggatcct taagaccagt cagtggttgc tc                                32

<210> SEQ ID NO 58
<211> LENGTH: 29
<212> TYPE: DNA
<213> ORGANISM: Artificial Sequence
<220> FEATURE:
<223> OTHER INFORMATION: Forward primer for KRS

<400> SEQUENCE: 58
gtcgaattct gatggcggcc gtgcaggcg                                    29

<210> SEQ ID NO 59
<211> LENGTH: 34
<212> TYPE: DNA
<213> ORGANISM: Artificial Sequence
<220> FEATURE:
<223> OTHER INFORMATION: Reverse primer for KRS

<400> SEQUENCE: 59
gtccccgggc tagacagaag tgccaactgt tgtg                              34

<210> SEQ ID NO 60
<211> LENGTH: 30
<212> TYPE: DNA
<213> ORGANISM: Artificial Sequence
<220> FEATURE:
<223> OTHER INFORMATION: Forward primer for RelA

<400> SEQUENCE: 60
ggactcgaga tggacgaact gttcccctc                                    30

<210> SEQ ID NO 61
<211> LENGTH: 36
<212> TYPE: DNA
<213> ORGANISM: Artificial Sequence
<220> FEATURE:
<223> OTHER INFORMATION: Reverse primer for RelA

<400> SEQUENCE: 61
gaaggatccc gttaggagct gatctgactc agcagg                            36

<210> SEQ ID NO 62
<211> LENGTH: 31
<212> TYPE: DNA
<213> ORGANISM: Artificial Sequence
<220> FEATURE:
<223> OTHER INFORMATION: Forward primer for IkB

<400> SEQUENCE: 62
gaagaattct gatgttccag gcggccgagc g                                 31

<210> SEQ ID NO 63
<211> LENGTH: 38
<212> TYPE: DNA
<213> ORGANISM: Artificial Sequence
<220> FEATURE:
<223> OTHER INFORMATION: Reverse primer for IkB

<400> SEQUENCE: 63
gaaggatccc gtcataaacg tcagacgctg gcctccaa                          38

<210> SEQ ID NO 64
<211> LENGTH: 33
```

<210> SEQ ID NO 64
<211> LENGTH: 33
<212> TYPE: DNA
<213> ORGANISM: Artificial Sequence
<220> FEATURE:
<223> OTHER INFORMATION: Forward primer for p50

<400> SEQUENCE: 64
gctgaattct gatggcagaa gatgatccat att                          33

<210> SEQ ID NO 65
<211> LENGTH: 34
<212> TYPE: DNA
<213> ORGANISM: Artificial Sequence
<220> FEATURE:
<223> OTHER INFORMATION: Reverse primer for p50

<400> SEQUENCE: 65
gctcccgggc ttaatgcttc atcccagcat taga                         34

<210> SEQ ID NO 66
<211> LENGTH: 33
<212> TYPE: DNA
<213> ORGANISM: Artificial Sequence
<220> FEATURE:
<223> OTHER INFORMATION: Forward primer for OmpA

<400> SEQUENCE: 66
gctgaattct gatgaaattg agtcgtattg cac                          33

<210> SEQ ID NO 67
<211> LENGTH: 30
<212> TYPE: DNA
<213> ORGANISM: Artificial Sequence
<220> FEATURE:
<223> OTHER INFORMATION: Reverse primer for OmpA

<400> SEQUENCE: 67
gctggatcct tattgagctg ctgcaggagc                              30

<210> SEQ ID NO 68
<211> LENGTH: 31
<212> TYPE: DNA
<213> ORGANISM: Artificial Sequence
<220> FEATURE:
<223> OTHER INFORMATION: Forward primer for EEF1A

<400> SEQUENCE: 68
gctgaattct gatgggaaag gaaaagactc a                            31

<210> SEQ ID NO 69
<211> LENGTH: 31
<212> TYPE: DNA
<213> ORGANISM: Artificial Sequence
<220> FEATURE:
<223> OTHER INFORMATION: Reverse primer for EEF1A

<400> SEQUENCE: 69
gctggatccc gctatttagc cttctgagct t                            31

<210> SEQ ID NO 70
<211> LENGTH: 32
<212> TYPE: DNA
<213> ORGANISM: Artificial Sequence
<220> FEATURE:
<223> OTHER INFORMATION: Forward primer for FAM14B

<400> SEQUENCE: 70
gtcgaattct gatgggaaag gagagtggat gg					32

<210> SEQ ID NO 71
<211> LENGTH: 31
<212> TYPE: DNA
<213> ORGANISM: Artificial Sequence
<220> FEATURE:
<223> OTHER INFORMATION: Reverse primer for FAM14B

<400> SEQUENCE: 71
gtcggatccc gtcagctgga aggggtgaa c					31

<210> SEQ ID NO 72
<211> LENGTH: 32
<212> TYPE: DNA
<213> ORGANISM: Artificial Sequence
<220> FEATURE:
<223> OTHER INFORMATION: Forward primer for DDX31

<400> SEQUENCE: 72
gtcgaattct gatgttttct ccaaagaagc at					32

<210> SEQ ID NO 73
<211> LENGTH: 33
<212> TYPE: DNA
<213> ORGANISM: Artificial Sequence
<220> FEATURE:
<223> OTHER INFORMATION: Reverse primer for DDX31

<400> SEQUENCE: 73
gtcggatccc gttaaacttt ctgggaagtc ttg					33

<210> SEQ ID NO 74
<211> LENGTH: 32
<212> TYPE: DNA
<213> ORGANISM: Artificial Sequence
<220> FEATURE:
<223> OTHER INFORMATION: Forward primer for p53N

<400> SEQUENCE: 74
gtcgaattct catggaggag ccgcagtcag at					32

<210> SEQ ID NO 75
<211> LENGTH: 29
<212> TYPE: DNA
<213> ORGANISM: Artificial Sequence
<220> FEATURE:
<223> OTHER INFORMATION: Reverse primer for p53N

<400> SEQUENCE: 75
gtcggatcct cacacggggg gagcagcct					29

<210> SEQ ID NO 76
<211> LENGTH: 37
<212> TYPE: DNA
<213> ORGANISM: Artificial Sequence
<220> FEATURE:
<223> OTHER INFORMATION: Forward primer for mdm2N

<400> SEQUENCE: 76
gtcgaattct gatgtgcaat accaacatgt ctgtacc					37

<210> SEQ ID NO 77
<211> LENGTH: 33
<212> TYPE: DNA
<213> ORGANISM: Artificial Sequence

```
<220> FEATURE:
<223> OTHER INFORMATION: Reverse primer for mdm2N

<400> SEQUENCE: 77
gtcggatcct catactacca agttcctgta gat                                    33
```